United States Patent
Berry Ann

(10) Patent No.: US 12,251,226 B2
(45) Date of Patent: Mar. 18, 2025

(54) AMBULATORY MEDICAL DEVICE HAVING SENSORS WITH LOCALIZED DRIVEN GROUNDS

(71) Applicant: ZOLL Medical Corporation, Chelmsford, MA (US)

(72) Inventor: Nathan J. Berry Ann, Cranberry Township, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 200 days.

(21) Appl. No.: 17/692,967

(22) Filed: Mar. 11, 2022

(65) Prior Publication Data
US 2022/0287612 A1    Sep. 15, 2022

Related U.S. Application Data

(60) Provisional application No. 63/159,704, filed on Mar. 11, 2021.

(51) Int. Cl.
*A61B 5/305*    (2021.01)
*A61N 1/362*    (2006.01)
*A61N 1/365*    (2006.01)

(52) U.S. Cl.
CPC ............ *A61B 5/305* (2021.01); *A61N 1/3625* (2013.01); *A61N 1/365* (2013.01)

(58) Field of Classification Search
CPC ........ A61B 5/305; A61B 5/308; A61B 5/0245
See application file for complete search history.

(56) References Cited

U.S. PATENT DOCUMENTS

| | | | |
|---|---|---|---|
| 5,944,669 A | 8/1999 | Kaib | |
| 6,253,099 B1 | 6/2001 | Oskin et al. | |
| 7,974,689 B2 | 7/2011 | Volpe et al. | |
| 8,140,154 B2 | 3/2012 | Donnelly et al. | |
| 8,600,486 B2 | 12/2013 | Kaib et al. | |
| 8,676,313 B2 | 3/2014 | Volpe et al. | |
| 8,706,215 B2* | 4/2014 | Kaib | A61B 5/259 600/509 |
| 8,897,860 B2 | 11/2014 | Volpe et al. | |
| 11,559,238 B2 | 1/2023 | Lucci et al. | |
| 2015/0313501 A1 | 11/2015 | Shachar | |
| 2016/0367162 A1 | 12/2016 | Kaib et al. | |
| 2020/0022607 A1 | 1/2020 | Pratt et al. | |
| 2022/0094305 A1* | 3/2022 | Tang | A61B 5/28 |

OTHER PUBLICATIONS

BS EN 60529:1992+A2:2013, Degrees of protection provided by enclosures (IP Code) (Published Feb. 28, 2019) (56 pages).

\* cited by examiner

*Primary Examiner* — George R Evanisko
(74) *Attorney, Agent, or Firm* — Finch & Maloney PLLC

(57) ABSTRACT

An ambulatory cardiac device for improving a signal to noise profile of an electrocardiogram (ECG) signal of a patient is provided. The ambulatory cardiac device includes a plurality of active ECG electrodes disposed in a plurality of locations about a patient. Each active electrode can include an ECG electrode substrate configured to be in physical contact with skin of the patient, a local biasing substrate proximate to the ECG electrode substrate and configured to be in physical contact with the skin of the patient, and local biasing circuitry configured to provide a local biasing signal into a body of the patient via the local biasing substrate.

20 Claims, 20 Drawing Sheets

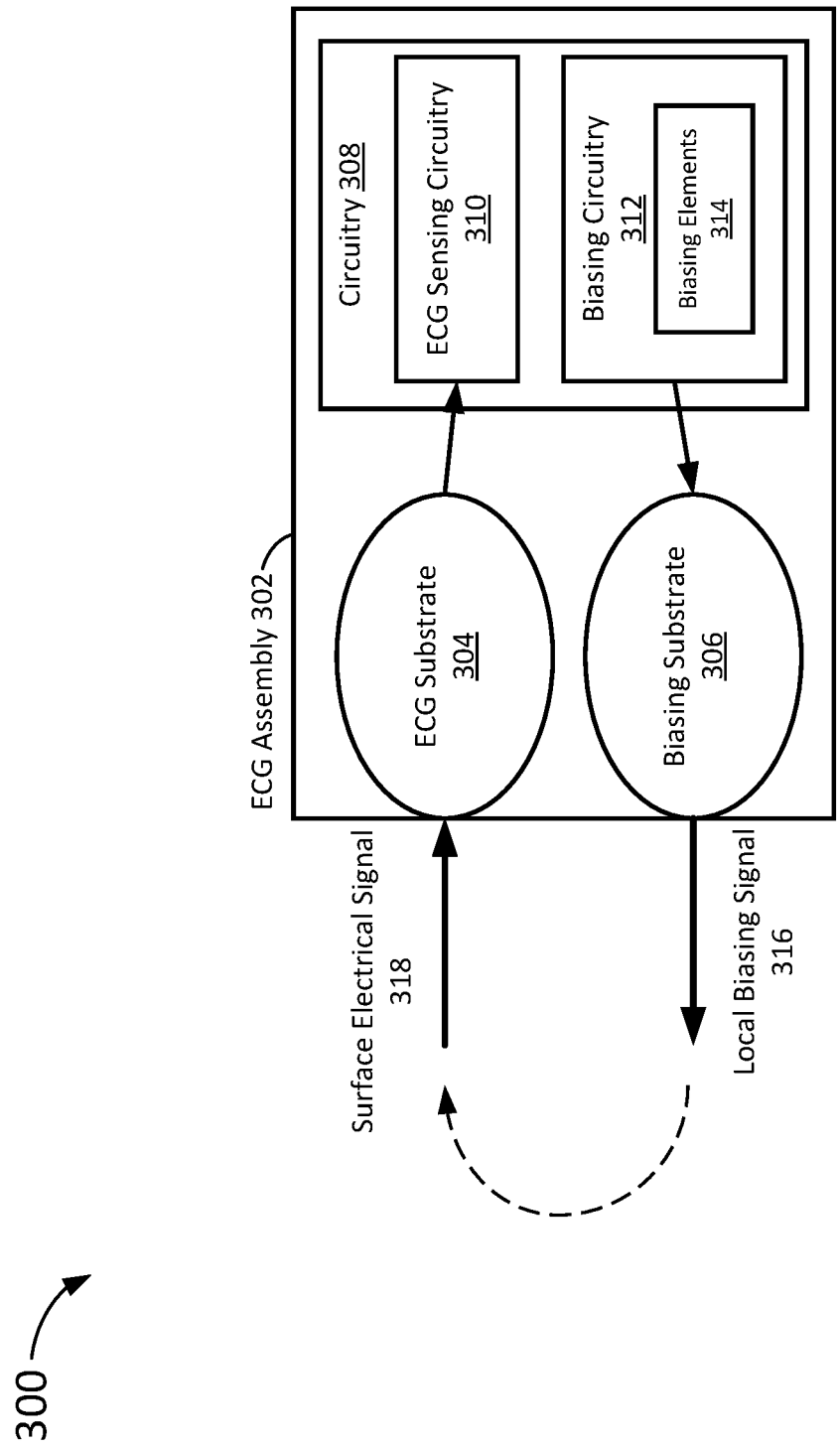

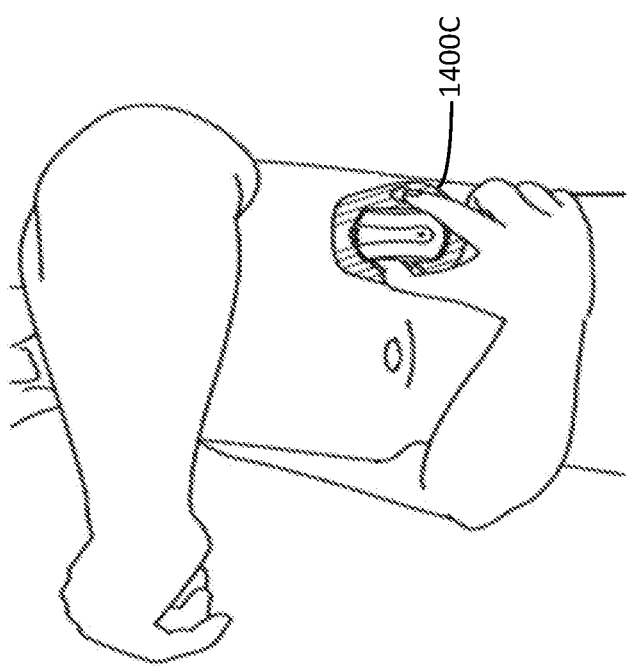
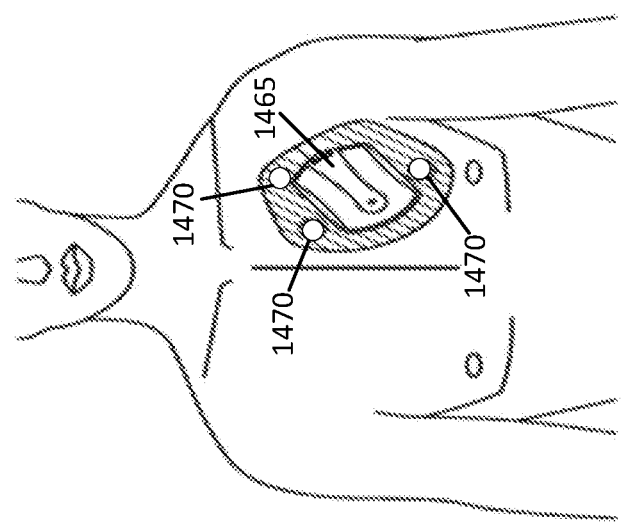
FIG. 14C

AMBULATORY MEDICAL DEVICE HAVING SENSORS WITH LOCALIZED DRIVEN GROUNDS

RELATED APPLICATION

This application claims priority under 35 U.S.C. § 119 (e) to U.S. Provisional Application Ser. No. 63/159,704, titled "AMBULATORY MEDICAL DEVICE HAVING SENSORS WITH LOCALIZED DRIVEN GROUNDS," filed Mar. 11, 2021, which is hereby incorporated herein by reference in its entirety.

BACKGROUND

The present disclosure is directed to sensors incorporated within a medical device for a variety of monitoring, diagnostic, and treatment purposes.

Heart failure, if left untreated, can lead to certain life-threatening arrhythmias. Both atrial and ventricular arrhythmias are common in patients with heart failure. One of the deadliest cardiac arrhythmias is ventricular fibrillation, which occurs when normal, regular electrical impulses are replaced by irregular and rapid impulses, causing the heart muscle to stop normal contractions. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity), result in the heart providing insufficient levels of blood flow to the brain and other vital organs for the support of life. It is generally useful to monitor heart failure patients to assess heart failure symptoms early and provide interventional therapies as soon as possible.

Patients who are at risk, have been hospitalized for, or otherwise are suffering from, adverse heart conditions can be prescribed a wearable cardiac monitoring and/or treatment device. In addition to the wearable device, the patient can also be given a battery charger and a set of rechargeable batteries. As the wearable device is generally prescribed for continuous or near-continuous use (e.g., only to be removed when bathing), the patient wears the device during all daily activities such as walking, sitting, climbing stairs, resting or sleeping, and other similar daily activities. Maintaining continuous or near-continuous use of the device as prescribed can be important for monitoring patient progress as well as providing treatment to the patient if needed.

SUMMARY

In at least one example, an ambulatory cardiac device for improving a signal to noise profile of an electrocardiogram (ECG) signal of a patient is provided. The ambulatory cardiac device includes a plurality of active ECG electrodes disposed in a plurality of locations about a patient. Each active electrode can include an ECG electrode substrate configured to be in physical contact with skin of the patient, a local biasing substrate proximate to the ECG electrode substrate and configured to be in physical contact with the skin of the patient, and local biasing circuitry configured to provide a local biasing signal into a body of the patient via the local biasing substrate.

Implementations of the ambulatory cardiac device for improving a signal to noise profile of an ECG signal of a patient can include one or more of the following features.

In examples, the ambulatory cardiac device can further include ECG sensing circuitry configured to sense a surface electrical signal from the ECG electrode substrate, the surface electrical signal including at least a portion of the local biasing signal. In some examples, the ambulatory cardiac device can further include a processor operably connected to the ECG sensing circuitry and configured to receive the surface electrical signals from the ECG sensing circuitries of the corresponding first and second ECG electrodes and determine an ECG signal of the patient based on the received surface electrical signals.

In examples of the ambulatory cardiac device, the local biasing circuitry can be configured to apply a constant biasing signal to the body of the patient. In some examples, the constant biasing signal has a voltage of one of about 0.5 volts, about 1.0 volt, about 1.5 volts, about 2.0 volts, about 2.5 volts, about 3.0 volts, about 3.5 volts, about 4.0 volts, or about 4.5 volts. In some examples, each of the plurality of active ECG electrodes can include a housing disposed proximate to the ECG electrode substrate for housing the ECG electrode substrate, the local biasing substrate, and the local biasing circuitry, the housing rated as IP67 in accordance with international standard EN 60529. In some examples, the ambulatory cardiac device can include a plurality of therapy electrodes for delivering one or more therapeutic pulses to the patient. In some examples, the ambulatory cardiac device can include an ECG acquisition box including a processor for determining the ECG signal of the patient based on a received surface electrical signal.

In some examples, the ambulatory cardiac device can include a controller operably coupled to each of the plurality of active ECG electrodes, the controller configured to determine an arrhythmia condition based on the ECG signal of the patient. In some examples, the controller is configured to control delivery one or more therapeutic pulses to the patient based on the determined arrhythmia condition. In some examples, the ambulatory cardiac device can further include at least one patient response button operably coupled to the controller. In some examples, the controller can be configured to control the delivery of the one or more therapeutic pulses to the patient if a patient response is not received via the at least one patient response button. In some examples, the ambulatory cardiac device can include a garment configured to be worn about a torso of the patient, and wherein plurality of active ECG electrodes are disposed within the garment.

In examples of the ambulatory cardiac device, the local biasing circuitry can be configured to apply a time-varying biasing signal based upon at least a portion of a surface electrical signal. In some examples, the time-varying biasing signal includes at least one of a time-varied current or a time-varied voltage. In some examples, the at least a portion of the surface electrical signal includes noise. In some examples, each of the plurality of active ECG electrodes include signal processing circuitry configured to determine the noise included in a surface electrical signal. In some examples, the time-varying biasing signal is based upon the determined noise included in the surface electrical signal. In some examples, the signal processing circuitry can be configured to cancel the noise from the surface electrical signal prior to a processor determining the ECG signal of the patient. In some examples, the signal processing circuitry can include a filter and amplifier circuit to process the surface electrical signal to isolate the noise. In some examples, each of the plurality of active ECG electrodes include a housing disposed proximate to the ECG electrode substrate for housing the ECG electrode substrate, the local biasing substrate, and the local biasing circuitry, the housing rated as IP67 in accordance with international standard EN 60529. In some examples, the ambulatory cardiac device can include a plurality of therapy electrodes for delivering one or more therapeutic pulses to the patient. In some examples, the ambulatory cardiac device can include an ECG acquisition box including a processor for determining the ECG signal of the patient based on a received surface electrical signal. In some examples, the ambulatory cardiac device can include a controller operably coupled to each of the plurality of active ECG electrodes, the controller configured to determine an arrhythmia condition based on the ECG signal of the patient. In some examples, the controller is configured to control delivery one or more therapeutic pulses to the patient based on the determined arrhythmia condition. In some examples, the ambulatory cardiac device can include at least one patient response button operably coupled to the controller. In some examples, the controller is configured to control delivery of one or more therapeutic pulses to the patient if a patient response is not received via the at least one patient response button. In some examples, the ambulatory cardiac device can include a garment configured to be worn about a torso of the patient, and wherein plurality of active ECG electrodes are disposed within the garment.

In examples of the ambulatory cardiac device, the local biasing signal can be configured to provide a grounding signal to the body of the patient to reduce noise in a surface electrical signal.

In examples of the ambulatory cardiac device, one or both of the ECG electrode substrate and the local biasing substrate can include a fabric material. In some examples, each of the plurality of active ECG electrodes includes a housing disposed proximate to the ECG electrode substrate for housing the ECG electrode substrate, the local biasing substrate, and the local biasing circuitry, the housing rated as IP67 in accordance with international standard EN 60529. In some examples, the ambulatory cardiac device can include a plurality of therapy electrodes for delivering one or more therapeutic pulses to the patient. In some examples, the ambulatory cardiac device can include an ECG acquisition box including a processor for determining the ECG signal of the patient based on a received surface electrical signal. In some examples, the ambulatory cardiac device can include a controller operably coupled to each of the plurality of active ECG electrodes, the controller configured to determine an arrhythmia condition based on the ECG signal of the patient. In some examples, the controller is configured to control delivery one or more therapeutic pulses to the patient based on the determined arrhythmia condition. In some examples, the ambulatory cardiac device can include at least one patient response button operably coupled to with the controller. In some examples, the controller is configured to control delivery of one or more therapeutic pulses to the patient if a patient response is not received via the at least one patient response button. In some examples, the ambulatory cardiac device can include a garment configured to be worn about a torso of the patient, and wherein plurality of active ECG electrodes are disposed within the garment. In some examples, the fabric material includes one or more flexible conductive fibers configured to provide an electrical contact with the patient.

In examples of the ambulatory cardiac device, each of the plurality of active ECG electrodes further can include an analog-to-digital converter operably coupled to the ECG electrode substrate and configured to convert at least a portion of a surface electrical signal to a digital surface electrical signal for transmitting to a processor.

In examples of the ambulatory cardiac device, each of the plurality of active ECG electrodes can include dry ECG electrodes. In some examples, each of the plurality of active ECG electrodes can include a housing disposed proximate to the ECG electrode substrate for housing the ECG electrode substrate, the local biasing substrate, and the local biasing circuitry, the housing rated as IP67 in accordance with international standard EN 60529. In some examples, the ambulatory cardiac device can include a plurality of therapy electrodes for delivering one or more therapeutic pulses to the patient. In some examples, the ambulatory cardiac device can include an ECG acquisition box including a processor for determining the ECG signal of the patient based on a received surface electrical signal. In some examples, the ambulatory cardiac device can include a controller operably coupled to each of the plurality of active ECG electrodes, the controller configured to determine an arrhythmia condition based on the ECG signal of the patient. In some examples, the controller is configured to control delivery one or more therapeutic pulses to the patient based on the determined arrhythmia condition. In some examples, the ambulatory cardiac device can include at least one patient response button operably coupled to the controller. In some examples, the controller is configured to control delivery of one or more therapeutic pulses to the patient if a patient response is not received via the at least one patient response button. In some examples, the ambulatory cardiac device can include a garment configured to be worn about a torso of the patient, and wherein the plurality of active ECG electrodes are disposed within the garment.

In examples of the ambulatory cardiac device, the local biasing substrate being proximate to the ECG electrode substrate includes the local biasing substrate substantially surrounding the ECG electrode substrate. In some examples, each of the plurality of active ECG electrodes includes a housing disposed proximate to the ECG electrode substrate for housing the ECG electrode substrate, the local biasing substrate, and the local biasing circuitry, the housing rated as IP67 in accordance with international standard EN 60529. In some examples, the ambulatory cardiac device can include a plurality of therapy electrodes for delivering one or more therapeutic pulses to the patient. In some examples, the ambulatory cardiac device can include an ECG acquisition box including a processor for determining the ECG signal of the patient based on a received surface electrical signal. In some examples, the ambulatory cardiac device can include a controller operably coupled to each of the plurality of active ECG electrodes, the controller configured to determine an arrhythmia condition based on the ECG signal of the patient. In some examples, the controller is configured to control delivery one or more therapeutic pulses to the patient based on the determined arrhythmia condition. In some examples, the ambulatory cardiac device can include at least one patient response button operably coupled to the controller. In some examples, the controller can be configured to control delivery of one or more therapeutic pulses to the patient if a patient response is not received via the at least one patient response button. In some examples, the ambulatory cardiac device can include a garment configured to be worn about a torso of the patient, and wherein the plurality of active ECG electrodes are disposed within the garment.

In examples of the ambulatory cardiac device, the local biasing substrate being proximate to the ECG electrode substrate can include the local biasing substrate being disposed adjacent the ECG electrode substrate on a fabric material.

In examples, the ambulatory cardiac device can include a shared driven ground electrode configured to aggregate surface electrical signals to derive a common mode rejection signal and inject the common mode rejection signal into the body of the patient. In some examples, each of the plurality of active ECG electrodes includes a housing disposed proximate to the ECG electrode substrate for housing the ECG electrode substrate, the local biasing substrate, and the local biasing circuitry, the housing rated as IP67 in accordance with international standard EN 60529. In some examples, the ambulatory cardiac device can include a plurality of therapy electrodes for delivering one or more therapeutic pulses to the patient. In some examples, the ambulatory cardiac device can include an ECG acquisition box including a processor for determining the ECG signal of the patient based on a received surface electrical signal. In some examples, the ambulatory cardiac device can include a controller operably coupled to each of the plurality of active ECG electrodes, the controller configured to determine an arrhythmia condition based on the ECG signal of the patient. In some examples, the controller is configured to control delivery one or more therapeutic pulses to the patient based on the determined arrhythmia condition. In some examples, the ambulatory cardiac device can include at least one patient response button operably coupled to the controller. In some examples, the controller is configured to control delivery of one or more therapeutic pulses to the patient if a patient response is not received via the at least one patient response button. In some examples, the ambulatory cardiac device can include a garment configured to be worn about a torso of the patient, and wherein the plurality of active ECG electrodes are disposed within the garment.

In examples, the ambulatory cardiac device can include a feedback loop circuit coupled between the ECG electrode substrate and the local biasing substrate. In some examples, the feedback loop circuit includes an inverting integrator circuit. In some examples, the ambulatory cardiac device can include an amplifier configured to output an amplified surface electrical signal. In some examples, the ambulatory cardiac device can include an amplifier configured to output an amplified surface electrical signal and a feedback loop circuit configured to receive the amplified surface electrical signal, invert the amplified surface electrical signal, integrate the inverted amplified surface electrical signal, and output the integrated signal to the local bias substrate. In some examples, each of the plurality of active ECG electrodes includes a housing disposed proximate to the ECG electrode substrate for housing the ECG electrode substrate, the local biasing substrate, and the local biasing circuitry, the housing rated as IP67 in accordance with international standard EN 60529. In some examples, the ambulatory cardiac device can include a plurality of therapy electrodes for delivering one or more therapeutic pulses to the patient. In some examples, the ambulatory cardiac device can include an ECG acquisition box including a processor for determining the ECG signal of the patient based on the received surface electrical signals. In some examples, the ambulatory cardiac device can include a controller operably coupled to each of the plurality of active ECG electrodes, the controller configured to determine an arrhythmia condition based on the ECG signal of the patient. In some examples, the controller is configured to control delivery one or more therapeutic pulses to the patient based on the determined arrhythmia condition. In some examples, the ambulatory cardiac device can include at least one patient response button operably coupled to the controller. In some examples, the controller is configured to control delivery of one or more therapeutic pulses to the patient if a patient response is not received via the at least one patient response button. In some examples, the ambulatory cardiac device can include a garment configured to be worn about a torso of the patient, and wherein the plurality of active ECG electrodes are disposed within the garment.

In another example, an ambulatory cardiac device having active ECG electrodes with local electronics for improving a signal to noise profile of an ECG signal of a patient is provided. The ambulatory cardiac device includes a first active ECG electrode, the first active ECG electrode including a first ECG electrode with associated first local electronics, a second active ECG electrode, the second active ECG electrode including a second ECG electrode with associated second local electronics, and a processor operably connected to the first and second active ECG electrodes. Each one of first and second active ECG electrodes includes an ECG electrode substrate configured to be in physical contact with skin of the patient, a local biasing substrate proximate to the ECG electrode substrate and configured to be in physical contact with the skin of the patient, and circuitry operably coupled to the ECG electrode substrate and the local biasing substrate. The circuitry includes local biasing circuitry configured to provide a local biasing signal into a body of the patient via the local biasing substrate and ECG sensing circuitry configured to sense a surface electrical signal from the ECG electrode substrate, the surface electrical signal including at least a portion of the local biasing signal. The processor is configured to receive the surface electrical signals from the ECG sensing circuitries of the corresponding first and second ECG electrodes and determine an ECG signal of the patient based on the received surface electrical signals.

Implementations of the ambulatory cardiac device having active ECG electrodes with local electronics for improving a signal to noise profile of an ECG signal of a patient can include one or more of the following features.

In examples, the ambulatory cardiac device can include third and fourth ECG electrode assemblies.

In examples of the ambulatory cardiac device, the circuitry is integrated into a printed circuit assembly.

In examples of the ambulatory cardiac device, the local biasing circuitry is configured to apply a constant biasing signal to the body of the patient. In some examples, the constant biasing signal has a voltage of one of about 0.5 volts, about 1.0 volt, about 1.5 volts, about 2.0 volts, about 2.5 volts, about 3.0 volts, about 3.5 volts, about 4.0 volts, or about 4.5 volts.

In examples of the ambulatory cardiac device, each of the first and second active ECG electrodes include a housing disposed proximate to the ECG electrode substrate for housing the first local electronics and the second local electronics, the housing rated as IP67 in accordance with international standard EN 60529.

In examples, the ambulatory cardiac device can include a plurality of therapy electrodes for delivering one or more therapeutic pulses to the patient.

In examples, the ambulatory cardiac device can include an ECG acquisition box including the processor for determining the ECG signal of the patient based on the received surface electrical signals.

In examples, the ambulatory cardiac device can include a controller operably coupled to the processor, the controller configured to determine an arrhythmia condition based on the ECG signal of the patient. In some examples, the controller is configured to control delivery one or more therapeutic pulses to the patient based on the determined arrhythmia condition. In some examples, the ambulatory cardiac device can include at least one patient response button operably coupled to the controller. In some examples, the controller is configured to control the delivery of the one or more therapeutic pulses to the patient if a patient response is not received via the at least one patient response button. In some examples, the ambulatory cardiac device can include a garment configured to be worn about a torso of the patient, and wherein the first and second ECG electrodes and associated first and second local electronics are disposed within the garment.

In examples of the ambulatory cardiac device, the local biasing circuitry can be configured to apply a time-varying biasing signal based upon at least a portion of the surface electrical signal. In some examples, the time-varying biasing signal includes at least one of a time-varied current or a time-varied voltage. In some examples, the at least a portion of the surface electrical signal includes noise. In some examples, each of the first and second local electronics include signal processing circuitry configured to determine the noise included in the surface electrical signals. In some examples, the time-varying biasing signal is based upon the determined noise included in the surface electrical signals. In some examples, the signal processing circuitry is configured to cancel the noise from the surface electrical signal prior to the processor determining the ECG signal of the patient. In some examples, the signal processing circuitry of each of the first and second active ECG electrodes includes a filter and amplifier circuit to process the surface electrical signal to isolate the noise. In some examples, each of the first and second active ECG electrodes include a housing disposed proximate to the ECG electrode substrate for housing the first local electronics and the second local electronics, the housing rated as IP67 in accordance with international standard EN 60529. In some examples, the ambulatory cardiac device can include a plurality of therapy electrodes for delivering one or more therapeutic pulses to the patient. In some examples, the ambulatory cardiac device can include an ECG acquisition box including the processor for determining the ECG signal of the patient based on the received surface electrical signals. In some examples, the ambulatory cardiac device can include a controller operably coupled to the processor, the controller configured to determine an arrhythmia condition based on the ECG signal of the patient. In some examples, the controller can be configured to control delivery one or more therapeutic pulses to the patient based on the determined arrhythmia condition. In some examples, the ambulatory cardiac device can include at least one patient response button operably coupled to the controller. In some examples, the controller can be configured to control the delivery of the one or more therapeutic pulses to the patient if a patient response is not received via the at least one patient response button. In some examples, the ambulatory cardiac device can include a garment configured to be worn about a torso of the patient, and wherein the first and second ECG electrodes and associated first and second local electronics are disposed within the garment.

In examples of the ambulatory cardiac device, the local biasing signal is configured to provide a grounding signal to the body of the patient to reduce noise in the surface electrical signal.

In examples of the ambulatory medical device, one or both of the ECG electrode substrate and the local biasing substrate includes a fabric material. In some examples, each of the first and second active ECG electrodes include a housing disposed proximate to the ECG electrode substrate for housing the first local electronics and the second local electronics, the housing rated as IP67 in accordance with international standard EN 60529. In some examples, the ambulatory cardiac device can include a plurality of therapy electrodes for delivering one or more therapeutic pulses to the patient. In some examples, the ambulatory cardiac device can include an ECG acquisition box including the processor for determining the ECG signal of the patient based on the received surface electrical signals. In some examples, the ambulatory cardiac device can include a controller operably coupled to the processor, the controller configured to determine an arrhythmia condition based on the ECG signal of the patient. In some examples, the controller is configured to control delivery one or more therapeutic pulses to the patient based on the determined arrhythmia condition. In some examples, the ambulatory cardiac device can include at least one patient response button operably coupled to the controller. In some examples, the controller is configured to control the delivery of the one or more therapeutic pulses to the patient if a patient response is not received via the at least one patient response button. In some examples, the ambulatory cardiac device can include a garment configured to be worn about a torso of the patient, and wherein the first and second ECG electrodes and associated first and second local electronics are disposed within the garment. In some examples, the fabric material includes one or more flexible conductive fibers configured to provide an electrical contact with the patient.

In examples of the ambulatory cardiac device, each of the first and second local electronics further includes an analog-to-digital converter operably coupled to the ECG sensing circuitry and configured to convert at least a portion of the surface electrical signal to a digital surface electrical signal for transmitting to the processor.

In examples of the ambulatory cardiac device, the first and second ECG electrodes include dry ECG electrodes. In some examples, each of the first and second active ECG electrodes include a housing disposed proximate to the ECG electrode substrate for housing the first local electronics and the second local electronics, the housing rated as IP67 in accordance with international standard EN 60529. In some examples, the ambulatory cardiac device can include a plurality of therapy electrodes for delivering one or more therapeutic pulses to the patient. In some examples, the ambulatory cardiac device can include an ECG acquisition box including the processor for determining the ECG signal of the patient based on the received surface electrical signals. In some examples, the ambulatory cardiac device can include a controller operably coupled to the processor, the controller configured to determine an arrhythmia condition based on the ECG signal of the patient. In some examples, the controller is configured to control delivery one or more therapeutic pulses to the patient based on the determined arrhythmia condition. In some examples, the ambulatory cardiac device can include at least one patient response button operably coupled to the controller. In some examples, the controller is configured to control the delivery of the one or more therapeutic pulses to the patient if a patient response is not received via the at least one patient response button. In some examples, the ambulatory cardiac device can include a garment configured to be worn about a torso of the patient, and wherein the first and second ECG electrodes and associated first and second local electronics are disposed within the garment.

In examples of the ambulatory cardiac device, the local biasing substrate being proximate to the ECG electrode substrate can include the local biasing substrate substantially surrounding the ECG electrode substrate. In some examples, each of the first and second active ECG electrodes include a housing disposed proximate to the ECG electrode substrate for housing the first local electronics and the second local electronics, the housing rated as IP67 in accordance with international standard EN 60529. In some examples, the ambulatory cardiac device can include a plurality of therapy electrodes for delivering one or more therapeutic pulses to the patient.

In some examples, the ambulatory cardiac device can include an ECG acquisition box including the processor for determining the ECG signal of the patient based on the received surface electrical signals. In some examples, the ambulatory cardiac device can include a controller operably coupled to the processor, the controller configured to determine an arrhythmia condition based on the ECG signal of the patient. In some examples, the controller is configured to control delivery one or more therapeutic pulses to the patient based on the determined arrhythmia condition. In some examples, the ambulatory cardiac device can include at least one patient response button operably coupled to the controller. In some examples, the controller is configured to control the delivery of the one or more therapeutic pulses to the patient if a patient response is not received via the at least one patient response button. In some examples, the ambulatory cardiac device can include a garment configured to be worn about a torso of the patient, and wherein the first and second ECG electrodes and associated first and second local electronics are disposed within the garment.

In examples of the ambulatory cardiac device, the local biasing substrate being proximate to the ECG electrode substrate can include the local biasing substrate being disposed adjacent the ECG electrode substrate on a fabric material.

In examples, the ambulatory cardiac device can include a shared driven ground electrode configured to aggregate the surface electrical signals to derive a common mode rejection signal and inject the common mode rejection signal into the body of the patient. In some examples, each of the first and second active ECG electrodes include a housing disposed proximate to the ECG electrode substrate for housing the first local electronics and the second local electronics, the housing rated as IP67 in accordance with international standard EN 60529. In some examples, the ambulatory cardiac device can include a plurality of therapy electrodes for delivering one or more therapeutic pulses to the patient. In some examples, the ambulatory cardiac device can include an ECG acquisition box including the processor for determining the ECG signal of the patient based on the received surface electrical signals. In some examples, the ambulatory cardiac device can include a controller operably coupled to the processor, the controller configured to determine an arrhythmia condition based on the ECG signal of the patient. In some examples, the controller is configured to control delivery one or more therapeutic pulses to the patient based on the determined arrhythmia condition. In some examples, the ambulatory cardiac device can include at least one patient response button operably coupled to the controller. In some examples, the controller can be configured to control the delivery of the one or more therapeutic pulses to the patient if a patient response is not received via the at least one patient response button. In some examples, the ambulatory cardiac device can include a garment configured to be worn about a torso of the patient, and wherein the first and second ECG electrodes and associated first and second local electronics are disposed within the garment.

In examples, the ambulatory cardiac device can include a feedback loop circuit coupled between the ECG electrode substrate and the local biasing substrate. In some examples, the feedback loop circuit includes an inverting integrator circuit. In some examples, the ambulatory cardiac device can include an amplifier configured to output an amplified surface electrical signal. In some examples, the ambulatory cardiac device can include an amplifier configured to output an amplified surface electrical signal and a feedback loop circuit configured to receive the amplified surface electrical signal, invert the amplified surface electrical signal, integrate the inverted amplified surface electrical signal, and output the integrated signal to the local bias substrate. In some examples, each of the first and second active ECG electrodes includes a housing disposed proximate to the ECG electrode substrate for housing the first local electronics and the second local electronics, the housing rated as IP67 in accordance with international standard EN 60529. In some examples, the ambulatory cardiac device can include a plurality of therapy electrodes for delivering one or more therapeutic pulses to the patient. In some examples, the ambulatory cardiac device can include an ECG acquisition box including the processor for determining the ECG signal of the patient based on the received surface electrical signals. In some examples, the ambulatory cardiac device can include a controller operably coupled to the processor, the controller configured to determine an arrhythmia condition based on the ECG signal of the patient. In some examples, the controller is configured to control delivery one or more therapeutic pulses to the patient based on the determined arrhythmia condition. In some examples, the ambulatory cardiac device can include at least one patient response button operably coupled to the controller. In some examples, the controller is configured to control the delivery of the one or more therapeutic pulses to the patient if a patient response is not received via the at least one patient response button. In some examples, the ambulatory cardiac device can include a garment configured to be worn about a torso of the patient, and wherein the first and second ECG electrodes and associated first and second local electronics are disposed within the garment.

In examples, the ambulatory cardiac device can include a main printed circuit assembly operably coupled to the printed circuit assemblies of the first and second local electronics, the main printed circuit assembly configured to receive analog surface electrical signals from the printed circuit assemblies of the first and second local electronics, convert the analog surface electrical signals into digitized surface electrical signals, and provide the digitized surface electrical signals to the processor.

In examples, the ambulatory cardiac device can include an array of ECG electrodes and associated local electronics, the array including the first and second ECG electrodes and associated first and second local electronics, wherein the processor is configured to selectively power two or more ECG electrodes of the array of ECG electrodes for use in determining the ECG signal of the patient. In some examples, each of the first and second active ECG electrodes include a housing disposed proximate to the ECG electrode substrate for housing the first local electronics and the second local electronics, the housing rated as IP67 in accordance with international standard EN 60529. In some examples, the ambulatory cardiac device can include a plurality of therapy electrodes for delivering one or more therapeutic pulses to the patient. In some examples, the ambulatory cardiac device can include an ECG acquisition box including the processor for determining the ECG signal of the patient based on the received surface electrical signals. In some examples, the ambulatory cardiac device can include a controller operably coupled to the processor, the controller configured to determine an arrhythmia condition based on the ECG signal of the patient. In some examples, the controller is configured to control delivery one or more therapeutic pulses to the patient based on the determined arrhythmia condition. In some examples, the ambulatory cardiac device can include at least one patient response button operably coupled to the controller. In some examples, the controller is configured to control the delivery of the one or more therapeutic pulses to the patient if a patient response is not received via the at least one patient response button. In some examples, the ambulatory cardiac device can include a garment configured to be worn about a torso of the patient, and wherein the first and second ECG electrodes and associated first and second local electronics are disposed within the garment.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples and are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIGS. 3A and 3B illustrates a sample sensor assembly including a steady local driven ground in accordance with an example of the present disclosure.

FIGS. 14A-14D illustrate sample ambulatory medical devices that may be prescribed to a heart failure patient in accordance with an example of the present disclosure.

DETAILED DESCRIPTION

As summarized above, example wearable ECG monitoring systems disclosed herein are directed to active ECG sensing electrode assemblies that include a localized driven ground implemented as, for example, a local biasing signal. By implementing a localized driven ground at each individual active ECG sensing electrode, noise and other similar signal degrading components can be reduced due to close proximity between a local biasing substrate that is configured to output the driven ground signal and an ECG substrate that is configured to detect at least a portion of the driven ground signal.

High-performance ECG monitoring systems can include a Right Leg Drive (RLD) or driven ground electrode that serves various functions. For example, the driven ground electrode acts to ground the patient to the medical device to reduce noise on signals obtained by the device such as skin surface electrical signals that are analyzed by the device to determine one or more ECG metrics for the patient. Additionally, the driven ground electrode helps to improve common mode rejection, which is important for 60 Hz noise rejection, which is an IEC60601-2-47 standard requirement. As such, by providing a common driven ground electrode, ECG monitoring systems act to reduce overall noise and provide a universal common mode rejection signal for processing of the skin surface electrical signals as obtained by the monitoring device.

In wearable ECG monitoring systems, noise and similar signal characteristics can degrade overall signal quality. Further, wires that connect the ECG electrodes to RLD and/or common mode rejection circuitry have associated lengths that result in relatively long driven ground loops that cause an unwanted increase in noise. For example, such wires have a length and associated impedance that can affect the driven ground signal. Similarly, for example, as flexible conductors such as fabric-based conductors that electrically connect the active ECG electrodes with RLD and/or common mode rejection circuitry can stretch and cause impedance changes and noise injection resulting from motion during use of the monitoring device. Such effects are another source of motion artifact that can affect the overall signal quality of the signals obtained by the wearable ECG monitoring device. Additionally, when considering the path of the common mode signal through the patient's body, the total length of the driven ground loop can exceed several feet, thereby increasing the potential for unwanted noise affecting the overall signal quality of the signals obtained by the wearable ECG monitoring device.

Figure 2:
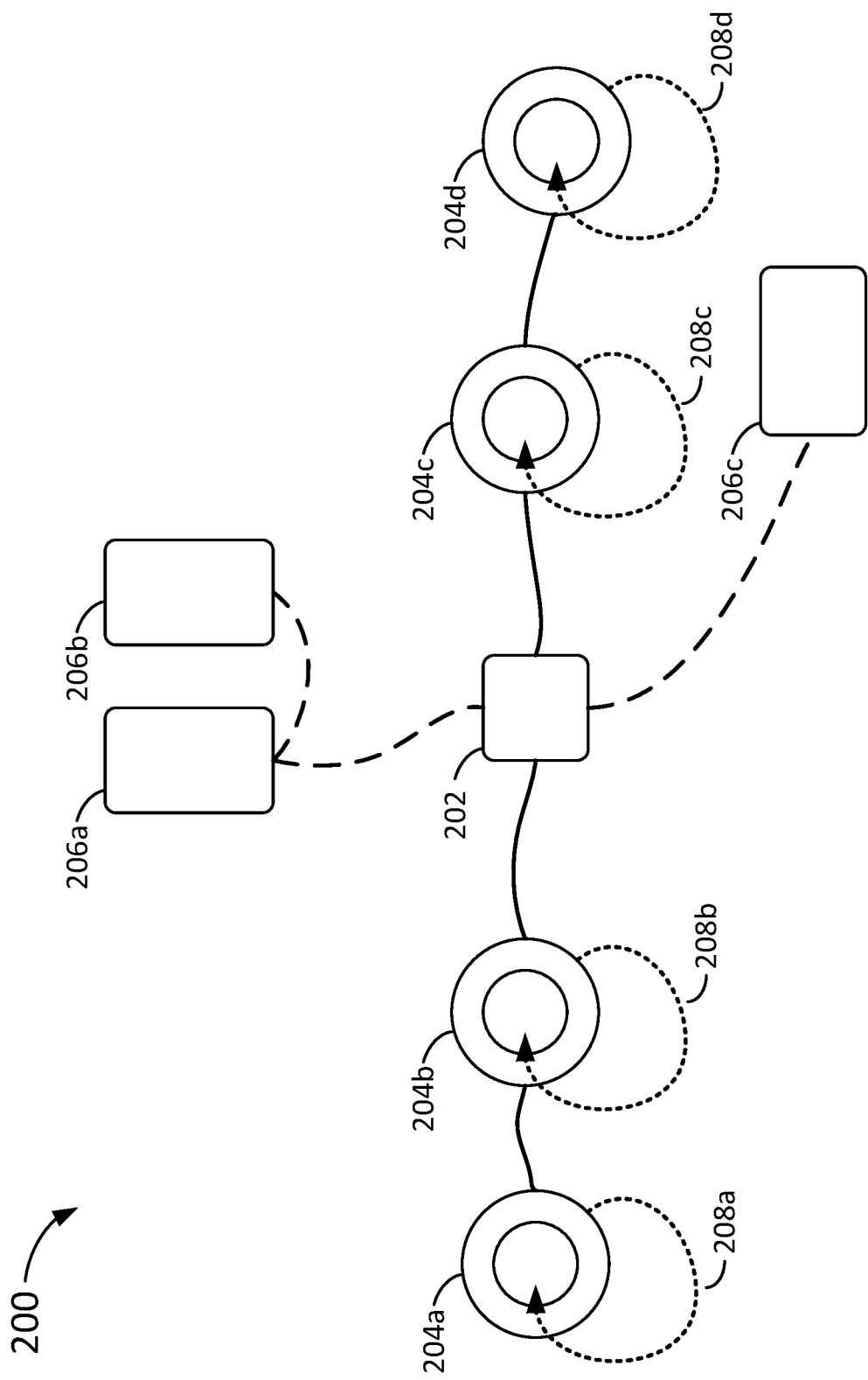
FIG. 2 illustrates a sample wearable cardiac device including sensors having local driven grounds in accordance with an example of the present disclosure.

In some example wearable ECG monitoring systems as described herein, disadvantages associated with wires coupling ECG electrodes to RLD and/or common mode rejection circuitry are reduced as a result of the localized driven ground signals. As the size of the ground signal loop for each individual sensing electrode is reduced, so too is the noise that accumulates on the signal between transmission into the patient's body and detection of the signal by the sensing electrode. For example, the arrangement as shown in FIG. 2 and described below can provide for reduced sized ground signal loops. To implement such an arrangement, examples as described herein include sensing electrodes that are configured to both generate a local biasing signal, transmit the local biasing signal into the patient via a biasing substrate, detect surface electrical signals of the patient by a ECG substrate positioned proximate to a debiasing substrate, and process the surface electrical signals wherein the surface electrical signals include at least a portion of the local biasing signal.

In some examples, the local biasing signal is a steady-state signal that is continually output by the biasing substrate. The steady-state biasing signal can be generated or otherwise output such that the surface electrical signals are centered about a particular voltage range of interest. In other examples, the local biasing signal can be a variable signal that is continually output by the biasing substrate. The variable signal can be generated or otherwise output based upon at least a portion of the surface electrical signals as detected by the ECG substrate.

In some examples, the biasing substrate and the ECG substrate can be integrated into a single electrode component. For example, the biasing substrate can be formed as an outer ring configured to surround the inner ECG substrate. In other examples, one or more of the biasing substrate and the ECG substrate can be manufactured from a flexible material such as a fabric electrode including, for example, a conductive thread woven or otherwise arranged into a particular pattern. Independent of the design and positioning of the individual substrates, however, the close proximity of the biasing substrate and the ECG substrate can provide for reduced noise in the resulting sensed surface electrical signal as detected or otherwise received by the ECG substrate.

These examples, and various other similar examples that benefit from the techniques, processes, and approaches as provided herein, are described in additional detail below.

A patient having an elevated risk of sudden cardiac death, unexplained syncope, prior symptoms of heart failure, an ejection fraction of less than 45%, less than 35%, or other such threshold deemed of concern by a physician, and other similar patients in a state of degraded cardiac health can be prescribed specialized cardiac monitoring and treatment devices, such as a mobile cardiac telemetry (MCT) device, a wearable cardioverter-defibrillator (WCD), and/or an hospital wearable defibrillator (HWD). As described above, such medical devices can benefit from the incorporation of, or interoperation with, an adjustable garment.

Figure 1A:
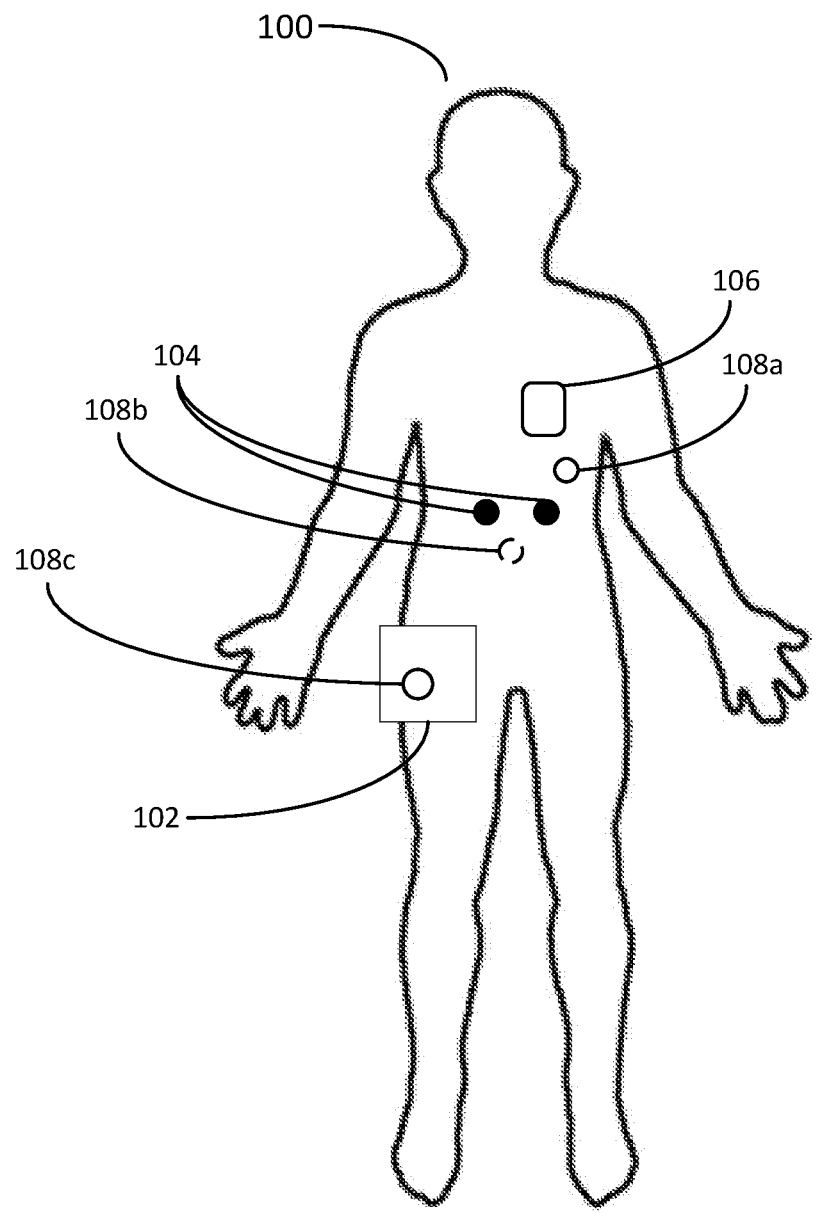
FIGS. 1A and 1B illustrate sample sensor arrangements in accordance with an example of the present disclosure.
Figure 1B:
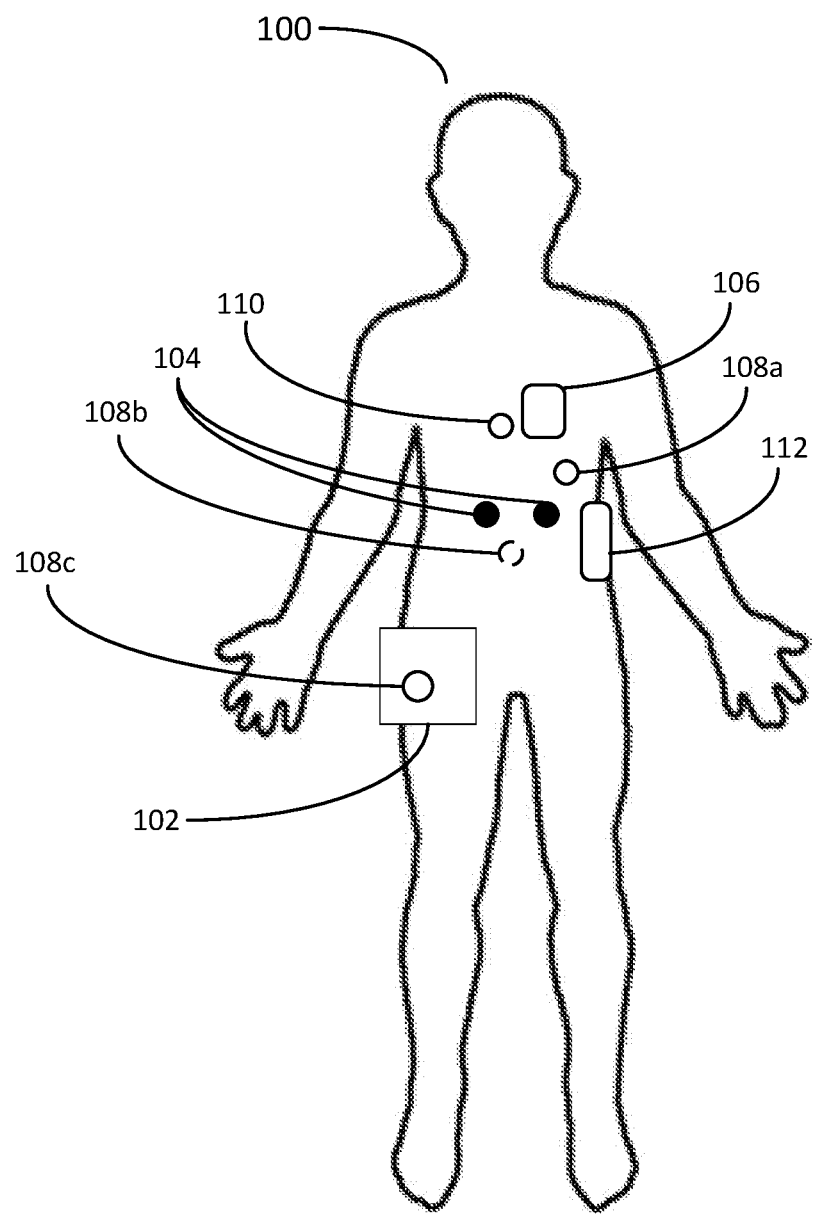

FIGS. 1A and 1B illustrate various examples of a patient 100 wearing medical devices that include one or more sensors (e.g., sensing electrodes, accelerometers, audio and/or vibrational sensors, radio frequency (RF) sensors, stretch or pressure sensors). As shown in FIG. 1A, the patient 100 can be prescribed an ambulatory medical device such as a WCD (or, for an in-hospital patient, an HWD). The WCD can include a controller 102 that is operably connected to one or more sensing electrodes 104 and therapy electrodes 106. Additional details of examples of the controller 102, sensing electrodes 104, and the therapy electrodes 106 can be found in the discussion of FIG. 6 below.

The WCD can also include one or more accelerometers or other motion sensors. As shown in FIG. 1A, the WCD can include three accelerometers 108a, 108b, and 108c (collectively referred to as accelerometers 108) positioned at various places on the body of patient 100. For example, accelerometer 108a can be positioned on the front of the chest of the patient 100, the accelerometer 108b can be positioned on the back of the patient 100, and the accelerometer 108c can be integrated into the controller 102. Each of the accelerometers 108 can be configured to measure movement associated with the patient 100 and to output an electrical signal indicating a direction and magnitude of the movement of the patient 100.

It should be noted that the number and arrangement of the accelerometers 108 as shown in FIG. 1A is by way of example only. In certain implementations, the number and position of the accelerometers 108 can vary. Additionally, when included in a device such as a WCD, one or more of the accelerometers 108 can be integrated into components of the WCD. For example, as noted above, the accelerometer 108c can be integrated into the controller 102 of the WCD. Similarly, one or more of accelerometers 108a and 108b can be integrated into one or more components of the WCD. For example, the front accelerometer 108a can be integrated into the therapy electrode 106, which is operably connected to the controller 102 and configured to provide a therapeutic shock to the patient 100. In some implementations, the accelerometer 108a can be integrated into one of the sensing electrodes 104, which are configured to measure electrical signals produced by the patient 100 that are indicative of cardiac activity of the patient 100. Similarly, accelerometer 108b can be integrated into one or more components of the WCD such as a connection node, at least one sensing electrode 104, the therapy electrode 106, and other similar components of the WCD as described herein. Alternatively or additionally, the one or more accelerometers 108 can be distinct components of the WCD.

In HWD implementations, the accelerometers can be integrated into one or more adhesive ECG sensing and/or therapy electrode patches. For example, a first accelerometer can be integrated into a first adhesive ECG sensing and/or therapy electrode patch and a second accelerometer can be integrated into a second adhesive ECG sensing and/or therapy electrode patch. Additional accelerometers can be disposed within a controller (similar to the controller 102 of a WCD) associated with the HWD.

In addition to accelerometers associated with a WCD as described above in regard to FIG. 1A, a patient such as the patient 100 can also wear additional sensors. As shown in FIG. 1B, the patient 100 can wear a vibrational sensor 110 that is configured to record bio-vibrational signals of the patient 100. For example, the vibrational sensor 110 can be configured to detect vibrations of the patient 100 that are associated with, for example, heart and lung activity. In certain implementations, the vibrational sensor 110 can be configured to detect cardiovibrational values including any one or all of S1, S2, S3, and S4. From these cardiovibrational values, certain heart vibration metrics or combinational metrics may be calculated, including any one or more of electromechanical activation time (EMAT), left ventricular systolic time (LVST), or percentage of left ventricular systolic time (% LVST). In some examples, the vibrational sensor 110 can be configured to detect vibrations from the cardiac system of the patient 100 and provide an output signal responsive to the detected cardiovibrational values. The vibrational sensor 110 can also include a multi-channel accelerometer, for example, a three-channel accelerometer configured to sense movement in each of three orthogonal axes such that patient movement/body position can be detected and correlated to detected cardiovibrational values. The vibrational sensor 110 can transmit information descriptive of the cardiovibrational values to, for example, a sensor interface for subsequent analysis as described below.

Additionally, the patient 100 can wear an RF sensor 112. For example, the RF sensor 112 can be configured to use RF-based techniques to assess fluid levels and accumulation in body tissue of the patient 100. For instance, the RF sensor 112 can be configured to measure fluid content in the lungs, typically for diagnosis and follow-up of pulmonary edema or lung congestion in heart failure patients. Similarly, the RF sensor can be configured to measure thoracic fluid content for the patient 100. In certain implementations, the RF sensor 112 can include one or more antennas configured to direct radio frequency waves through tissue of the patient 100 and measure output radio frequency signals in response to the waves that have passed through the tissue. In certain implementations, the output radio frequency signals include parameters indicative of a fluid level in the tissue. The RF sensor 112 can transmit information descriptive of the tissue fluid levels to a sensor interface for subsequent analysis as described below.

It should be noted that the placement and number of sensors as shown in FIGS. 1A and 1B are shown by way of example only. In actual implementation of the medical devices as described herein, the number and position of the sensors can vary based upon the type of patient monitoring and/or treatment to be performed and other various factors.

FIG. 2 illustrates system 200 including the components of a wearable medical device including, for example, a WCD as described herein. As shown in FIG. 2, the components of the wearable medical device can be operably connected to a node 202 including, for example, a belt node or other similar node configured to both receive signals from and transmit signals to the components of the wearable medical device. For example, as shown in FIG. 2, belt node 202 can be operably connected to a set of sensing electrodes 204a-204d. In certain implementations, if the wearable medical device includes treatment functionality, a set of therapy electrodes 206a-206c can also be operably coupled to the belt node 202. In some examples, the belt node 202 can be further coupled to a controller or another processing device configured to receive signals from the belt node 202, process the signals received from the belt node 202, and send control signals back to the belt node 202. As such, the belt node 202 can be configured to operate as an ECG acquisition node or box that is configured to determine an ECG signal of the patient based on a received surface electrical signal as received from each of the sensing electrodes 204a-204d as described herein.

As further shown in FIG. 2, and as taught herein, each of the sensing electrodes 204a-204d can be configured to include circuitry to generate and output a localized driven ground signal. As described herein, by providing each individual sensing electrode with the circuitry to generate and output a localized driven ground signal, overall system noise can be reduced as the individual ground loop size for each sensing electrode is reduced. Additionally, the multiple localized driven ground signals provide redundancy in the system as sensing electrodes can further detect localized driven ground signals from other sensing electrodes in the event of a malfunction of an individual electrode's ability to generate a localized driven ground signal. In other examples, the sensing electrodes can include sensed localized driven ground signals from other sensing electrodes when generating a common mode noise signal and, as a result of the combined common mode noise signal, reduce or otherwise eliminate system noise more efficiently and accurately.

Figure 3B:
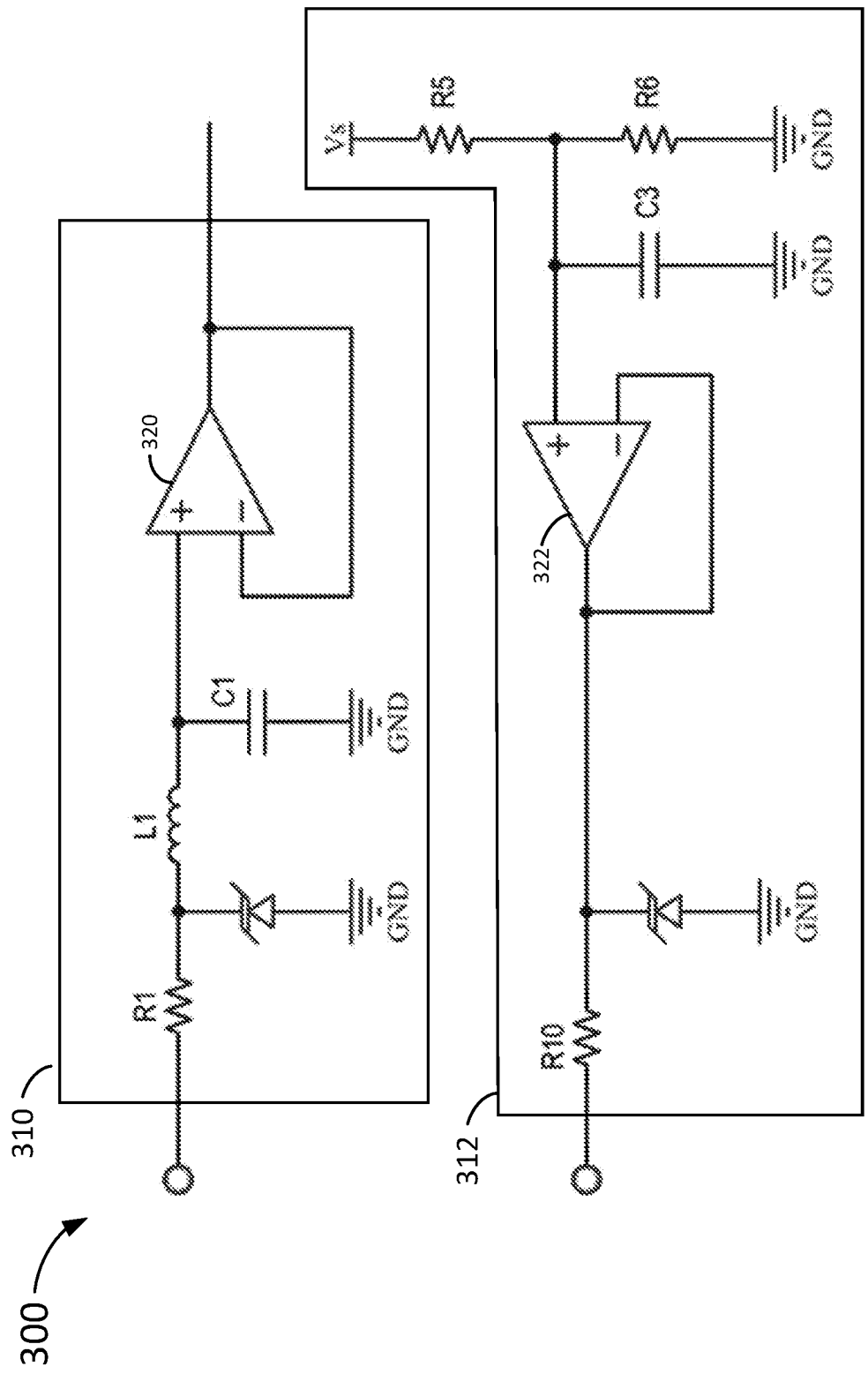

More specifically, as shown in FIG. 2 and described in greater detail in the discussion of FIGS. 3A and 3B, each of the sensing electrodes 204a-204d can include an ECG electrode substrate configured to be in physical contact with the skin of the patient and sense, detect, or otherwise receive one or more surface electrical signals from the patient. Additionally, each of the sensing electrodes 204a-204d can further include a local biasing substrate proximate to the ECG electrode substrate and also configured to be in physical contact with the skin of the patient. The local biasing substrate can be configured to provide a local biasing signal to the patient's body, the local biasing signal acting as a localized driven ground signal as described herein. For example, as shown in FIG. 2, sensing electrode 204a can be configured to transmit and receive localized driven ground signal 208a. Similarly, sensing electrode 204b can be configured to transmit and receive localized driven ground signal 208b, sensing electrode 204c can be configured to transmit and receive localized driven ground signal 208c, and sensing electrode 204d can be configured to transmit and receive localized driven ground signal 208d.

FIG. 3A illustrates system 300 including a more detailed schematic view of a sensing electrode such as one of sensing electrodes 204a-204d as shown in FIG. 2 and described above. For example, as shown in FIG. 3A, an ECG assembly 302 can include an ECG substrate 304 and a biasing substrate 306. In some examples, the ECG substrate 304 can be a dry substrate, e.g., a substrate that is not attached to the patient's skin by an adhesive or where contact is mediated by conductive gel. In an example scenario, a dry ECG substrate is placed directly on the skin and, as a result of the contact between the electrode and the skin, perspiration can accumulate on the electrode surface to provide an electrolytic connection with the patient. A dry ECG substrate can be constructed from a housing configured to hold various circuit components and a treated, anodized metal surface configured to contact the patient's skin. For example, the treated, anodized metal surface can be treated with a tantalum pentoxide coating.

Depending on the design, a dry ECG substrate can be configured to have a wide range of input impedances when in contact with a patient's skin. For example, the impedance as seen by the ECG substrate when in contact with the patient's skin can be in excess of 400 ohms, typically in the range of tens to hundreds of mega ohms. In certain implementations, the dry ECG substrate can have an impedance range of 400 ohms to 10 Megaohms. In some examples, a dry ECG substrate can be a high impedance electrode having an impedance range of 10 Megaohms to 100 Megaohms, 100 Megaohms to 1.0 Gigaohm, and 1.0 Gigaohm to 10 Gigaohms.

As described herein, the ECG substrate 304 can be configured to be in physical contact with the skin of the patient. Similarly, the biasing substrate 306 can also be configured to be in physical contact with the skin of the patient and positioned proximate to the ECG substrate 304 such that any signal transmitted or otherwise output by the biasing substrate 306 is detected and received by the ECG substate 304. Additionally, the ECG assembly 302 can include a circuitry 308. The circuitry 308 can be configured to receive signals to the biasing substrate 304, process the received signals, and output one or more signals to the biasing substrate 306. In certain implementations, the circuitry 308 can be implemented as a printed circuit assembly manufactured in or otherwise printed on a dedicated circuit board.

As further shown in FIG. 3A, the circuitry 308 can include an ECG sensing circuitry 310. The ECG sensing circuitry 310 can be electrically coupled to the ECG electrode substrate 304 and configured to receive one or more surface electrical signals as sensed or otherwise received by the ECG substrate 304. Similarly, the circuitry 308 can include a biasing circuitry 312. The biasing circuitry 312 can be electrically coupled to the biasing substrate 306 and configured to provide a local biasing signal to the biasing substrate 306 for transmission into the patient's body. In certain implementations, the biasing circuitry 312 can include one or more biasing elements 314 configured to condition the local biasing signal. For example, the biasing elements 314 can include one or more circuit elements such as resistors, capacitors, inductors, operational amplifiers, diodes, ground signals, voltage inputs, and other similar circuit elements.

As further shown in FIG. 3A, the biasing substrate 306 can be configured to output a local biasing signal 316 to the skin of the patient. The ECG substrate 304 can be configured to receive or otherwise sense a surface electrical signal 318. In some examples, the surface electrical signal 318 can include electrical signals generated by the body of the patient including, for example, signals indicative of cardiac activity of the patient as well as at least a portion of the local biasing signal 316 as output by the biasing substrate 306. Based upon the close proximity of the ECG substrate 304 and the biasing substrate 306, noise introduced into the surface electrical signal 318 as a result of the distance travelled by the local biasing signal 316 is reduced, thereby increasing the signal-to-noise ratio of the surface electrical signal 318 and the overall signal quality of the surface electrical signal 318.

In certain implementations, the biasing signal as output by the biasing substrate can be configured to be a steady-state signal. For example, the biasing circuitry can be configured to condition a steady voltage input and output a steady-state biasing signal. FIG. 3B illustrates a more detailed view of system 300 including particular circuit elements configured to process the surface electrical signal 318 as sensed or otherwise received by the ECG substrate 304, as well as to condition a steady-state biasing signal for output by the biasing substrate 306 as the local biasing signal 316.

More specifically, as shown in FIG. 3B, the ECG sensing circuitry 310 can include various circuit elements configured to condition the surface electrical signal 318 as sensed or otherwise received by the ECG substrate 304. For example, the ECG sensing circuitry 310 can include a resistor R1 sized appropriately to condition the surface electrical signal 318 and to provide patient isolation from the components of the ECG circuitry 310. In an example, R1 can have a resistance between about 50 kiloohms and 500 kiloohms. Additionally, the ECG sensing circuitry 310 can include an inductor L1 and capacitor C1 also sized appropriately to condition the surface electrical signal 318 and provide for a high frequency lowpass filter. For example, L1 can have an inductance of about 10 nanohenrys to about 10 microhenrys and C1 can have a capacitance of about 10 picofarads to about 1000 picofarads. The ECG sensing circuitry 310 can also include at least one operational amplifier 320. In certain implementations, the operational amplifier 320 can be configured to produce a high-gain output based upon the conditioned surface electrical signal 318. For example, based upon the input and circuit components used to condition the inputs of the operational amplifier 320, the operational amplifier 320 can be configured to output a signal approximately equal to the patient's measured ECG signal (e.g., about 100 microvolts to about 5.0 millivolts) plus any noise as well as a DC voltage that is approximately equal to the biasing signal plus any offsets related to the skin/electrode interface (e.g., between about 100 millivolts to 1000 millivolts). The output of the operational amplifier 320 can be passed to, for example, a processor for further analysis and processing of the conditioned surface electrical signal 318 as described herein.

As further shown in FIG. 3B, the biasing circuitry 312 can also include various circuit elements configured to produce a steady-state biasing signal to be output as the local biasing signal 316. For example, the biasing circuitry 312 can include various resistors R5, R6, and R10 sized appropriately to condition an input steady voltage signal $V_s$ such as, for example, a 5.0 volt input. In an example, resistors R5 and R6 can have a resistance of between about 1.0 kiloohm and about 1.0 Megaohm. The combination of resistors R5 and R6 can form a voltage divider used to generate a localized bias voltage from the local supply voltage $V_s$. Resistor R10 can be included to protect circuitry from voltage caused by, for example, a defibrillation or other treatment event. Resistor R10 can have a resistance between about 1.0 kiloohm and about 100 kiloohms. In some examples, the resistor R10 can be replaced with a high-voltage switch configured to protect components of the biasing circuitry 312.

Additionally, the biasing circuitry can include at least one capacitor C3 sized appropriately to filter the localized bias voltage. In an example, C3 can have a capacitance of about 1.0 microfarad to about 50.0 microfarads. The biasing circuitry 312 can also include an operational amplifier 322 configured to produce a high-gain output based upon the localized bias voltage. In certain implementations, the operational amplifier 322 can be configured to produce a voltage equal to half of the supply voltage $V_s$ as well as the electrode half-cell potential for, for example, a silver/silver chloride electrode. For a dry electrode, the operational amplifier 322 can be configured to produce a signal between about 2.0 volts and 5.0 volts to account for variation in electrode offset during wear.

It should be noted that the input voltages as shown in FIG. 3B as included in the biasing circuitry 312 are shown by way of example only. In implementation, the input voltages can be selected or otherwise chosen based upon the expected voltage range of the surface electrical signals 318 as sensed or otherwise received by the ECG substrate 304. For example, if the desired voltage range of the surface electrical signals 318 is 0.0 to 5.0 volts, the input voltage can be selected such that the local biasing signal 316 is approximately half of the expected voltage range, in this example, 2.5 volts. By providing a local biasing signal 316 that is approximately half of the expected voltage range of the surface electrical signal 318, the local biasing signal 316 can act to center the surface electrical signal 318 about the appropriate and expected voltage range.

It should be noted that the 2.5 volts is selected as the voltage of the output local biasing signal by way of example only. In implementations, the voltage of the output local biasing signal can vary accordingly and include, for example, voltages including, but not limited to, 0.5 volts, 1.0 volt, 1.5 volts, 2.0 volts, 2.5 volts, 3.0 volts, 3.5 volts, 4.0 volts, and 4.5 volts. More generally, any voltage between o volts and the chosen supply voltage can be output as the local biasing signal as described herein.

In the arrangement as shown in FIGS. 3A and 3B, the bias substrate can drive a constant and steady-state bias voltage into the patient's body in close proximity to the ECG substrate. Such an approach can be implemented with active electrodes that include a digital front end including, for example, additional circuitry such as an analog-to-digital converter and microcontroller. For active electrodes, several feet of cable length can be omitted, thereby avoiding a source of signal noise that degrades or otherwise impacts the quality of the sensed ECG signals.

In addition to providing a steady-state local biasing signal, a sensor assembly as described herein can be configured to produce a variable local biasing signal using, for example, an inverting integrator circuit. For example, the biasing circuitry can use a conditioned version of the sensed surface electrical signals as an input rather than a fixed voltage input as shown in FIG. 3B and described above.

Figure 4A:
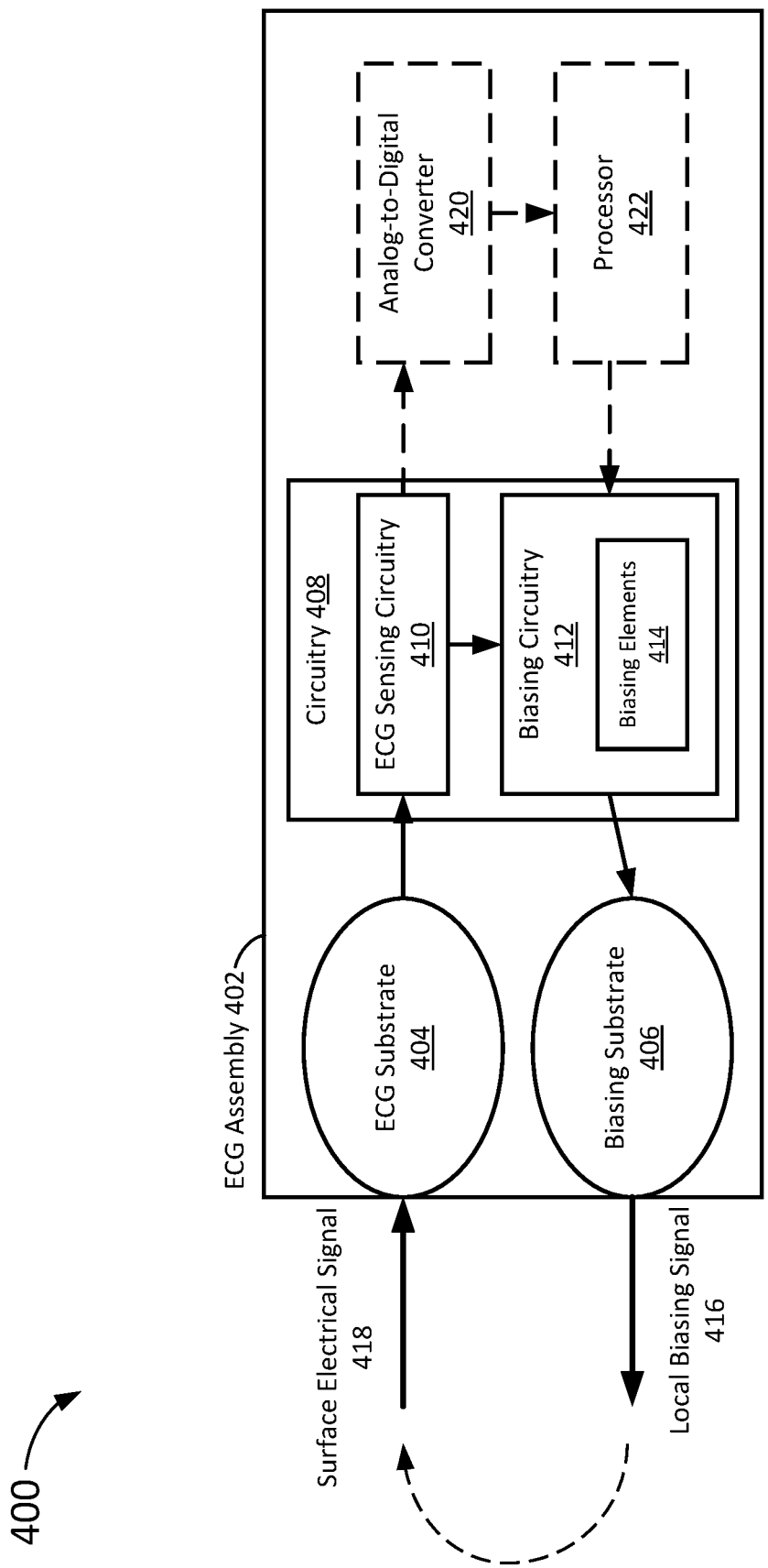
FIGS. 4A and 4B illustrates a sample sensor assembly including a variable local driven ground in accordance with an example of the present disclosure.

For example, FIG. 4A illustrates system 400 including a detailed schematic view of a sensing electrode assembly that includes a variable local biasing signal. For example, as shown in FIG. 4A, an ECG assembly 402 can include an ECG substrate 404 and a biasing substrate 406. As described herein, the ECG substrate 404 can be configured to be in physical contact with the skin of the patient. Similarly, the biasing substrate 406 can also be configured to be in physical contact with the skin of the patient and positioned proximate to the ECG substrate 404 such that any signal transmitted or otherwise output by the biasing substrate 406 is detected and received by the ECG substrate 404. Additionally, the ECG assembly 402 can include circuitry 408. The circuitry 408 can be configured to receive signals from the ECG substrate 404, process the received signals, and output one or more signals to the biasing substrate 406. In certain implementations, the circuitry 408 can be implemented as a printed circuit assembly manufactured in or otherwise printed on a dedicated circuit board.

As further shown in FIG. 4A, the circuitry 408 can include an ECG sensing circuitry 410. The ECG sensing circuitry 410 can be electrically coupled to ECG electrode substrate 404 and configured to receive one or more surface electrical signals as sensed or otherwise received by the ECG substrate 404. Similarly, the circuitry 408 can include a biasing circuitry 412. The biasing circuitry 412 can be electrically coupled to the biasing substrate 406 and configured to provide a local biasing signal to the biasing substrate 406 for transmission into the patient's body. In certain implementations, the biasing circuitry 412 can include one or more biasing elements 414 configured to condition the local biasing signal. For example, the biasing elements 414 can include one or more circuit elements such as resistors, capacitors, inductors, operational amplifiers, diodes, ground signals, voltage inputs, and other similar circuit elements. Additionally, as shown in FIG. 4A, the biasing circuitry 412 can be operably connected to the ECG sensing circuitry 410 and configured to receive one or more signals from the ECG sensing circuitry 410.

As further shown in FIG. 4A, the biasing substrate 406 is configured to output a local biasing signal 416 to the skin of the patient. The ECG substrate 404 can be configured to receive or otherwise sense a surface electrical signal 418. In some examples, the surface electrical signal 418 includes electrical signals generated by the body of the patient including, for example, signals indicative of cardiac activity of the patient as well as at least a portion of the local biasing signal 416 as output by the biasing substrate 406. Based upon the close proximity of the ECG substrate 404 and the biasing substrate 406, noise introduced into the surface electrical signal 418 as a result of the distance travelled by the local biasing signal 416 is reduced, thereby increasing the signal-to-noise ratio of the surface electrical signal 418 and the overall signal quality of the surface electrical signal 418.

In some examples, as further shown in FIG. 4A, the output of the ECG sensing circuitry can also be directed to an analog-to-digital converter 420. The converter 420 can be configured to receive the output of the ECG sensing circuitry 410 and convert the signal to a digital signal. The digital output of the converter 420 can be output to a processor 422. The processor 422 can be configured to generate a local biasing input signal based upon the digital signal and output the local biasing input signal to the biasing circuitry 412. In some examples, the output of the processor 422 can be a filtered pulse-width modulated signal. In some other examples, the processor can be configured to control a digital-to-analog converter to adjust the input to, for example, an operational amplifier as described below.

Figure 4B:
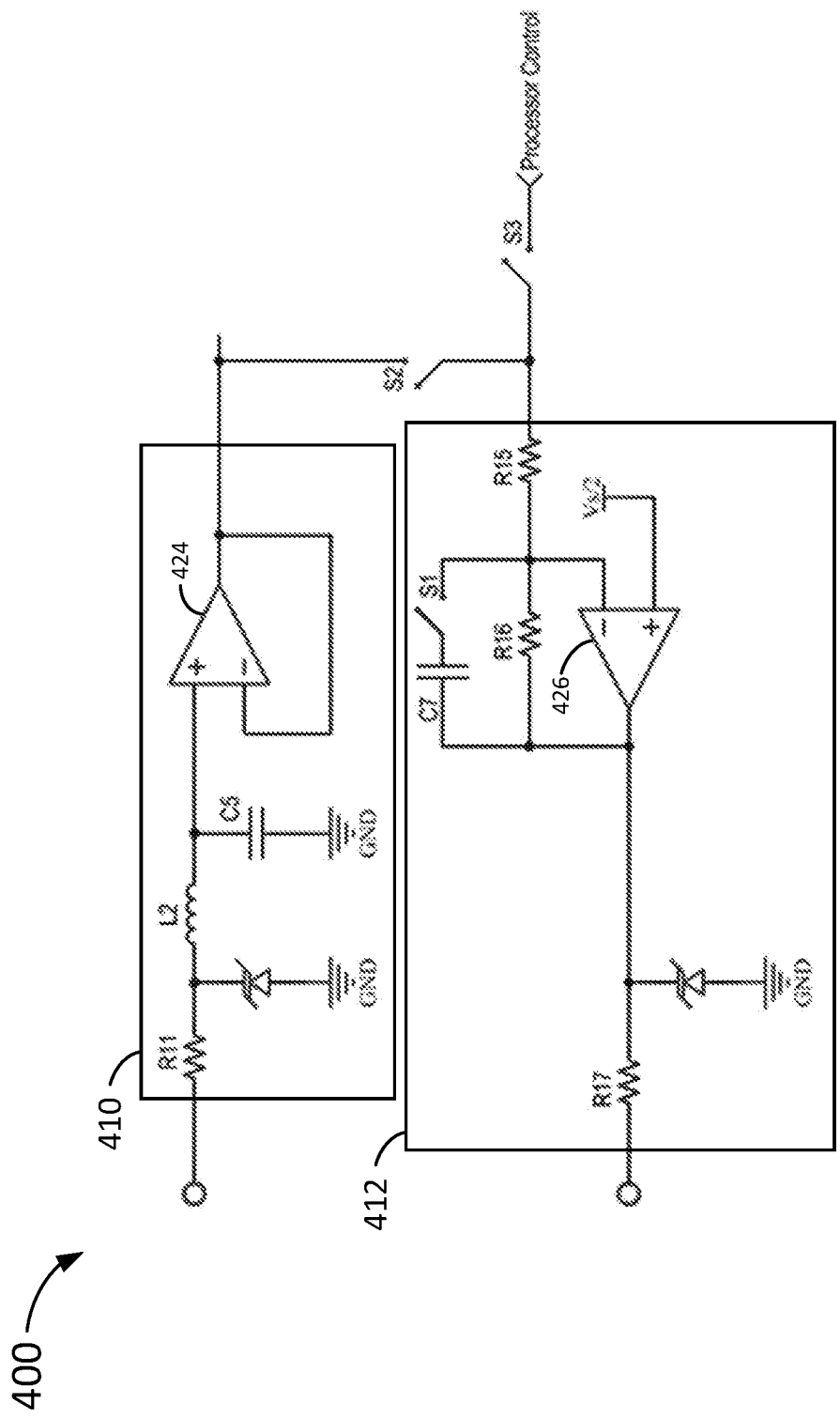

In certain implementations, the biasing signal as output by the biasing substrate can be configured to be a variable signal. For example, the biasing circuitry can be configured to condition a varying input received from the ECG sensing circuitry and to condition and output a variable biasing signal. FIG. 4B illustrates a more detailed view of the system 400 including particular circuit elements configured to process the surface electrical signal 418 as sensed or otherwise received by the ECG substrate 404, as well as to condition a variable biasing signal for output by the biasing substrate 406 as the local biasing signal 416.

More specifically, as shown in FIG. 4B, the ECG sensing circuitry 410 can include various circuit elements configured to condition the surface electrical signal 418 as sensed or otherwise received by the ECG substrate 404. For example, the ECG sensing circuitry 410 can include a resistor R11 sized appropriately to condition the surface electrical signal 418 and to provide patient isolation from the components of the ECG circuitry 410. In an example, R11 can have a resistance between about 50 kiloohms and 500 kiloohms. Additionally, the ECG sensing circuitry 410 can include an inductor L2 and capacitor C5 also sized appropriately to condition the surface electrical signal 418 and provide for a high frequency lowpass filter. For example, L2 can have an inductance of about 10 nanohenrys to about 10 microhenrys and C5 can have a capacitance of about 10 picofarads to about 1000 picofarads. The ECG sensing circuitry 410 can also include at least one operational amplifier 424. In certain implementations, the operational amplifier 424 can be configured to produce a high-gain output based upon the conditioned surface electrical signal 418. For example, based upon the input and circuit components used to condition the inputs of the operational amplifier 424, the operational amplifier 424 can be configured to output a signal approximately equal to the patient's measured ECG signal (e.g., about 100 microvolts to about 5.0 millivolts) plus any noise as well as a DC voltage that is approximately equal to the biasing signal plus any offsets related to the skin/electrode interface (e.g., between about 100 millivolts to 1000 millivolts). The output of the operational amplifier 424 can be passed to, for example, a processor for further analysis and processing of the conditioned surface electrical signal 418 as described herein.

As further shown in FIG. 4B, the output of the operational amplifier 424 can be passed to the biasing circuitry 412. The biasing circuitry 412 can include various circuit elements configured to produce a variable biasing signal based upon the output of the operational amplifier to be output as the local biasing signal 416. For example, the biasing circuitry 412 can include various resistors R15, R16, and R17 sized appropriately to condition an input steady voltage signal $V_s/2$ such as, for example, a 2.5 volt input. In an example, resistors R15 and R16 can have a resistance of between about 1.0 kiloohm and about 1.0 Megaohm. The combination of resistors R15 and R16 can form a voltage divider used to generate a localized bias voltage from the local supply voltage $V_s/2$. Resistor R17 can be included to protect circuitry from voltage caused by, for example, a defibrillation or other treatment event. Resistor R17 can have a resistance between about 1.0 kiloohm and about 100 kiloohms. In some examples, the resistor R17 can be replaced with a high-voltage switch configured to protect components of the biasing circuitry 412.

Additionally, the biasing circuitry can include at least one capacitor C7 sized appropriately to filter the localized bias voltage. In an example, C7 can have a capacitance of about 1.0 microfarad to about 50.0 microfarads. The biasing circuitry 412 can also include an operational amplifier 426 configured to produce a high-gain output based upon the localized bias voltage. In certain implementations, the operational amplifier 426 can be configured to produce a voltage equal to the supply voltage $V_s/2$ as well as the electrode half-cell potential for, for example, a silver/silver chloride electrode. For a dry electrode, the operational amplifier 426 can be configured to produce a signal between about 2.0 volts and 5.0 volts to account for variation in electrode offset during wear.

Additionally, as shown in FIG. 4B, the circuitry can include several switches S1, S2, and S3. Depending upon the state of each individual switch, the type of input signal and resulting output local bias signal 416 can be controlled. For example, if each of switches S1, S2, and S3 are open, this results in a stable constant DC bias applied to the biasing substrate 406 for output as the local biasing signal 416. In another example, if switches S1 and S2 are closed, and switch S3 is open, the output of the ECG sensing circuitry 410 is integrated into the local biasing signal 416. In another example, if switches S1 and S2 are open, and switch S3 is closed, a local processor (such as processor 422 as shown in FIG. 4A and described above) can control the input signal to the biasing circuitry 412 and the resulting local biasing signal 416 output by the biasing substrate 406 as described above. For example, as noted above, the local processor can be configured to output a filtered pulse-width modulated signal or to control a digital-to-analog converter to adjust the input to, for example, the operational amplifier 426 described herein.

The arrangement as shown in FIG. 4B provides for a variable biasing signal that varies in response to changes in the surface electrical signals as well as to potential input signals from a local processor. Such an arrangement provides for a feedback loop implemented as an inverting integrator. The integrator circuit inverts the output of the operational amplifier 424, integrates the signal, and sends back out to the biasing substrate as the variable biasing signal. Such an approach can cancel slow drifts in ECG electrode offset over time that can naturally occur through wear, after cleaning the sensing electrodes, applying lotion, and other similar patient activities that may impact the quality of the skin-interface connection. This approach can also help to avoid amplifier saturation or signal clipping that may otherwise occur at certain gain settings.

It should be noted that the variable biasing signal as discussed with regard to FIGS. 4A and 4B above is shown as a variable voltage signal by way of example only. In actual implementation, the variable biasing signal can be implemented as a time-varying signal that includes one of a variable current signal or a variable voltage signal as described above.

Figure 5:
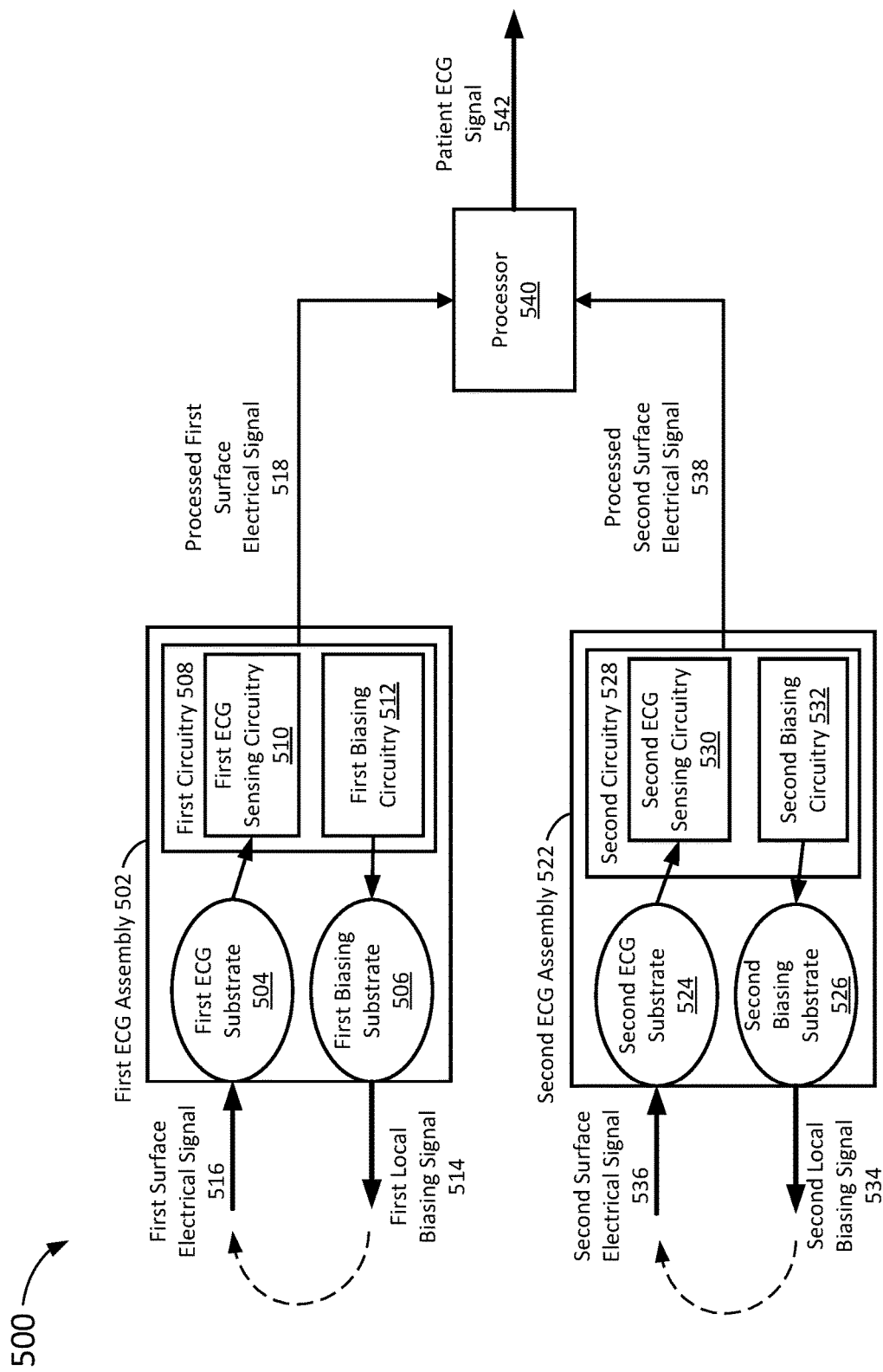
FIG. 5 illustrates a sample arrangement including multiple sensor assemblies having local driven grounds in accordance with an example of the present disclosure.

In certain examples, multiple sensor assemblies can be arranged into leads or sensor pairs, the outputs of which are used by a processor to determine one or more ECG metrics and an associated cardiac activity for a patient. For example, FIG. 5 illustrates a system 500 including two ECG assemblies as described herein. A first ECG assembly 502 can include a first ECG substrate 504 and a first biasing substrate 506. The first ECG assembly 502 can also include a first circuitry 508. The first circuitry 508 can include a first ECG sensing circuitry 510 as well as a first biasing circuitry 512. The first circuitry 508 can be configured to process and analyze signals received from the first ECG substrate 504 as well as to generate and condition a biasing signal for output by the first biasing substrate 506. For example, the first circuitry 508 can be configured to generate a steady-state biasing signal as described above, for example, in the discussion of FIG. 3B or a variable biasing signal as described above, for example, in the discussion of FIG. 4B.

As further shown in FIG. 5, the first biasing substrate 506 of first ECG assembly 502 can be configured to output a first local biasing signal 514. Additionally, the first ECG substrate 504 can be configured to sense or otherwise receive a first electrical signal 516 from the patient. In certain implementations, the first surface electrical signal 516 includes at least a portion of the first local biasing signal 514 as output by the first biasing substrate 506. Based upon the first electrical signal 516, the first circuitry 508 can be configured to output a conditioned and processed first surface electrical signal 518.

FIG. 5 further illustrates a second ECG assembly 522. The second ECG assembly 522 can include a second ECG substrate 524 and a second biasing substrate 526. The second ECG assembly 522 can also include a second circuitry 528. The second circuitry 528 can include second ECG sensing circuitry 530 as well as a second biasing circuitry 532. The second circuitry 528 can be configured to process and analyze signals received from the second ECG substrate 524 as well as to generate and condition a biasing signal for output by the second biasing substrate 526. For example, the second circuitry 528 can be configured to generate a steady-state biasing signal as described above in the discussion of FIG. 3B or a variable biasing signal as described above in the discussion of FIG. 4B.

As further shown in FIG. 5, the second biasing substrate 526 of the second ECG assembly 522 can be configured to output a second local biasing signal 534. Additionally, the second ECG substrate 524 can be configured to sense or otherwise receive a second electrical signal 536 from the patient. In certain implementations, the second surface electrical signal 536 includes at least a portion of the second local biasing signal 534 as output by the second biasing substrate 526. Based upon the second electrical signal 536, the second circuitry 528 can be configured to output a conditioned and processed second surface electrical signal 538.

As further shown in FIG. 5, a processor 540 can be configured to receive both the processed first surface electrical signal 518 and the processed second surface electrical signal 538. The processor 540 can be configured to further condition and process the received signals an output a patient ECG signal 542 for further analysis by, for example, a medical device controller as described herein. In certain implementations, the processor 540 can be integrated into a node such as belt node 202 as described herein above. In some examples, the processor 540 can be integrated into the medical device controller as described herein below. In other examples, an ECG assembly can be implemented as an active electrode that includes a local processor for conditioning the surface electrical signals directly at the sensing electrode. In such an example, the active electrode can be configured to output a signal similar to the patient ECG signal 542 for further processing by a medical device controller as described herein.

Figure 6:
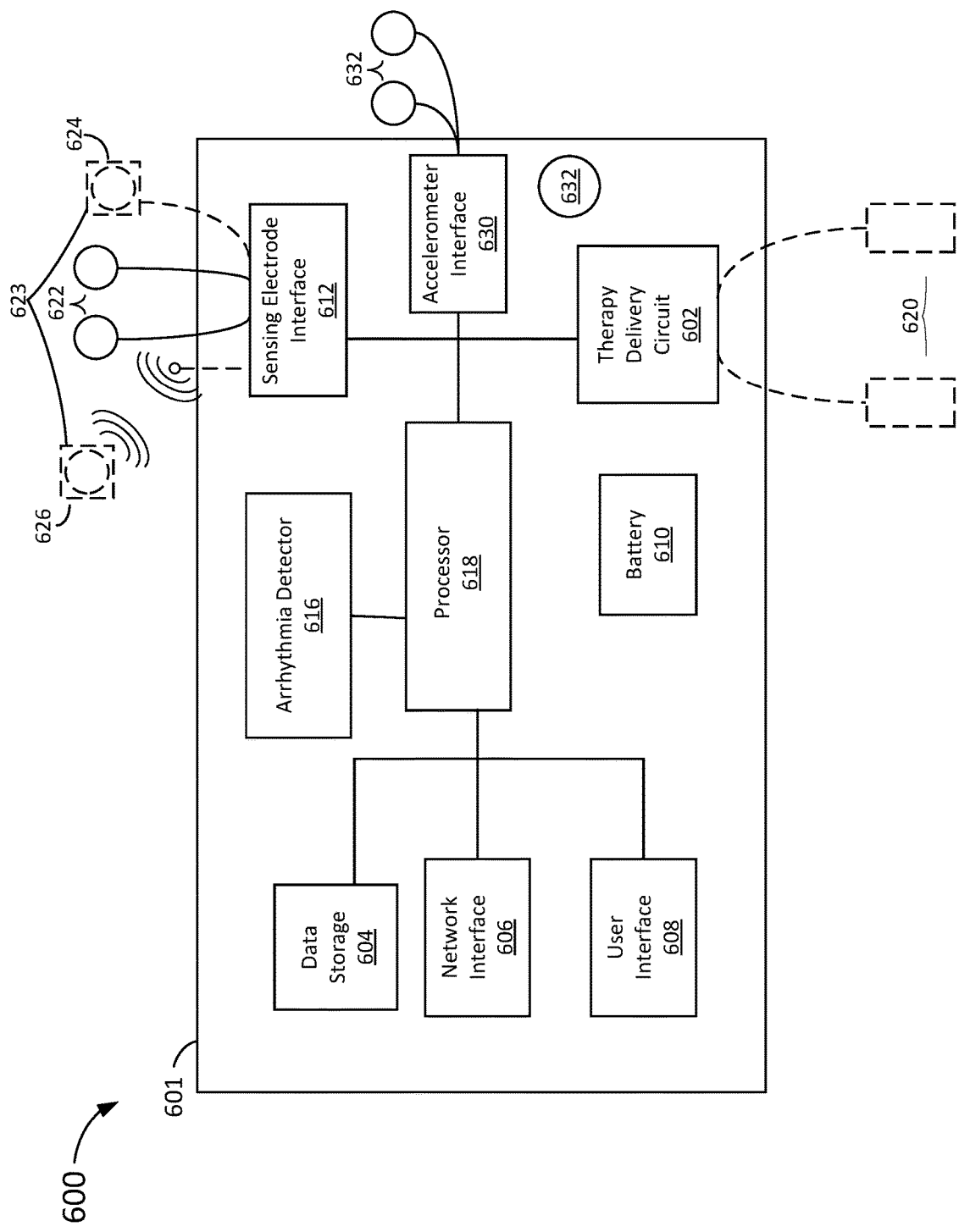
FIG. 6 illustrates a schematic view of a sample controller for a wearable medical device, in accordance with an example of the present disclosure.

FIG. 6 illustrates an example of a medical device controller 600 that is configured to control components of the medical devices described herein as well as process signals received from, for example, one or more sensing electrodes as described herein. A brief introduction applicable to medical controllers in general will now be provided with reference to FIG. 6. A more detailed description of some of the components of the medical device controller 600 is provided for additional context in a sample medical device discussion further below.

More specifically, FIG. 6 illustrates an example component-level view of the medical device controller 600 included in, for example, a wearable medical device such as a WCD or an HWD as described herein. As shown in FIG. 6, the medical device controller 600 can include a housing 601. The housing 601 can house a therapy delivery circuitry 602 configured to provide one or more therapeutic shocks to a patient via at least two therapy electrodes 620 (e.g., therapy electrode 106 and therapy electrodes 206a-206c as described above), a data storage 604, a network interface 606, a user interface 608, and at least one rechargeable battery 610 (e.g., within a battery chamber configured for such purpose). The housing 601 can be further configured to house a sensor interface 612 (e.g., to interface with both ECG sensing electrodes 622 (e.g., sensing electrodes 104 and sensing electrodes 204a-204d as described above) and non-ECG physiological sensors 623 such as vibrational sensors (e.g., vibrational sensor 110), lung fluid sensors (e.g., RF sensor 112), infrared and near-infrared-based pulse oximetry sensor, and blood pressure sensors, among others), a cardiac event detector 616, and at least one processor 618.

In some examples, the patient monitoring medical device can include a medical device controller that includes like components as those described above but that does not include the therapy delivery circuitry 602 and the therapy electrodes 620 (shown in dotted lines). That is, in certain implementations, the medical device can include only ECG monitoring components and not provide therapy to the patient. In such implementations, which may be referred to as MCT devices, the construction of the patient monitoring medical device is similar in many respects to the medical device controller 600 but need not include the therapy delivery circuitry 602 and associated therapy electrodes 620.

Figure 7:
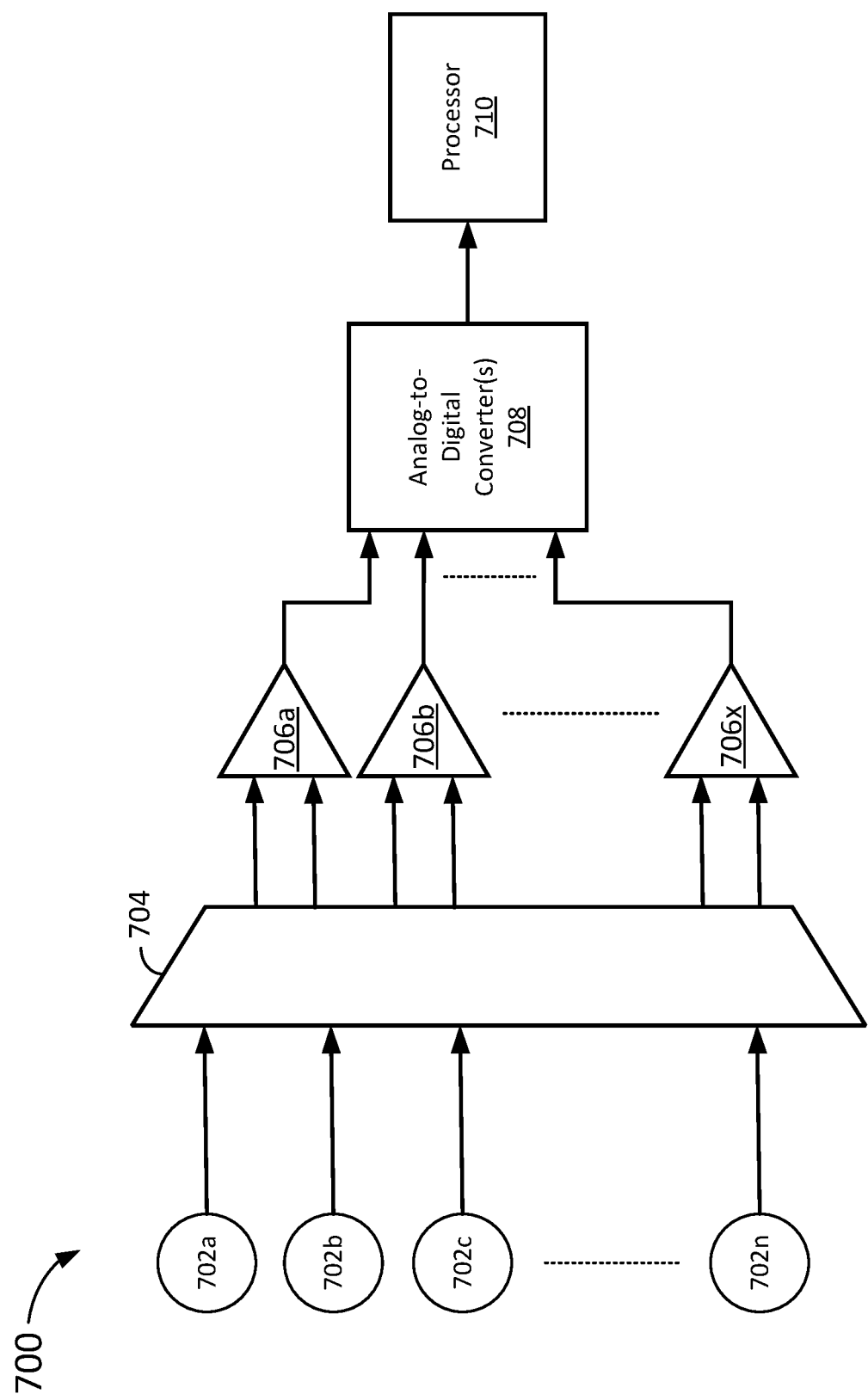
FIG. 7 illustrates a sample system for determining sensor leads in accordance with an example of the present disclosure.

In addition to providing a localized driven ground signal as described herein, the concepts as described can further be used to provide for selective lead forming and power management of an array of active electrodes. For example, FIG. 7 illustrates a system 700 that can be used to dynamically select sensing electrode leads. More specifically, as shown in FIG. 7, the system 700 can include a set of sensing electrodes 702a, 702b, 702c, through 702n. Each of the sensing electrodes can be operably coupled to a lead select switch 704. The lead select switch 704 can be configured to receive the output of the sensing electrodes and determine one or more electrode pairs based upon an analysis of the output. The lead select switch 704 can be further configured to output signals received from the sensing electrodes to one or more amplifiers 706a through 706x. For example, the amplifiers 706a through 706x can be implemented as operational amplifiers or instrumentation amplifiers. The amplifiers 706a through 706x can be configured to amplify and filter the signals to form one or more lead outputs for each sensing electrode lead as output by the lead select switch. The outputs of the amplifiers 706a, 706b, through 706x can be transferred to one or more analog-to-digital converters 708 for processing and conversion to a digital output for transmission to, and processing by, a processor 710.

For example, based upon an analysis of the output of each sensing electrode, a processing device operably coupled to the lead select switch 704 can determine that sensing electrode 702a and sensing electrode 702b are to be coupled as a sensing electrode lead. As such, lead select switch 704 can be configured to output signals received from electrode 702a and sensing electrode 702b to the amplifier 706a. The amplifier 706a can be configured to condition and filter the signal and output an electrode lead signal to the analog-to-digital converter 708 for processing and conversion to a single digital signal for further processing by processor 710.

Figure 8:
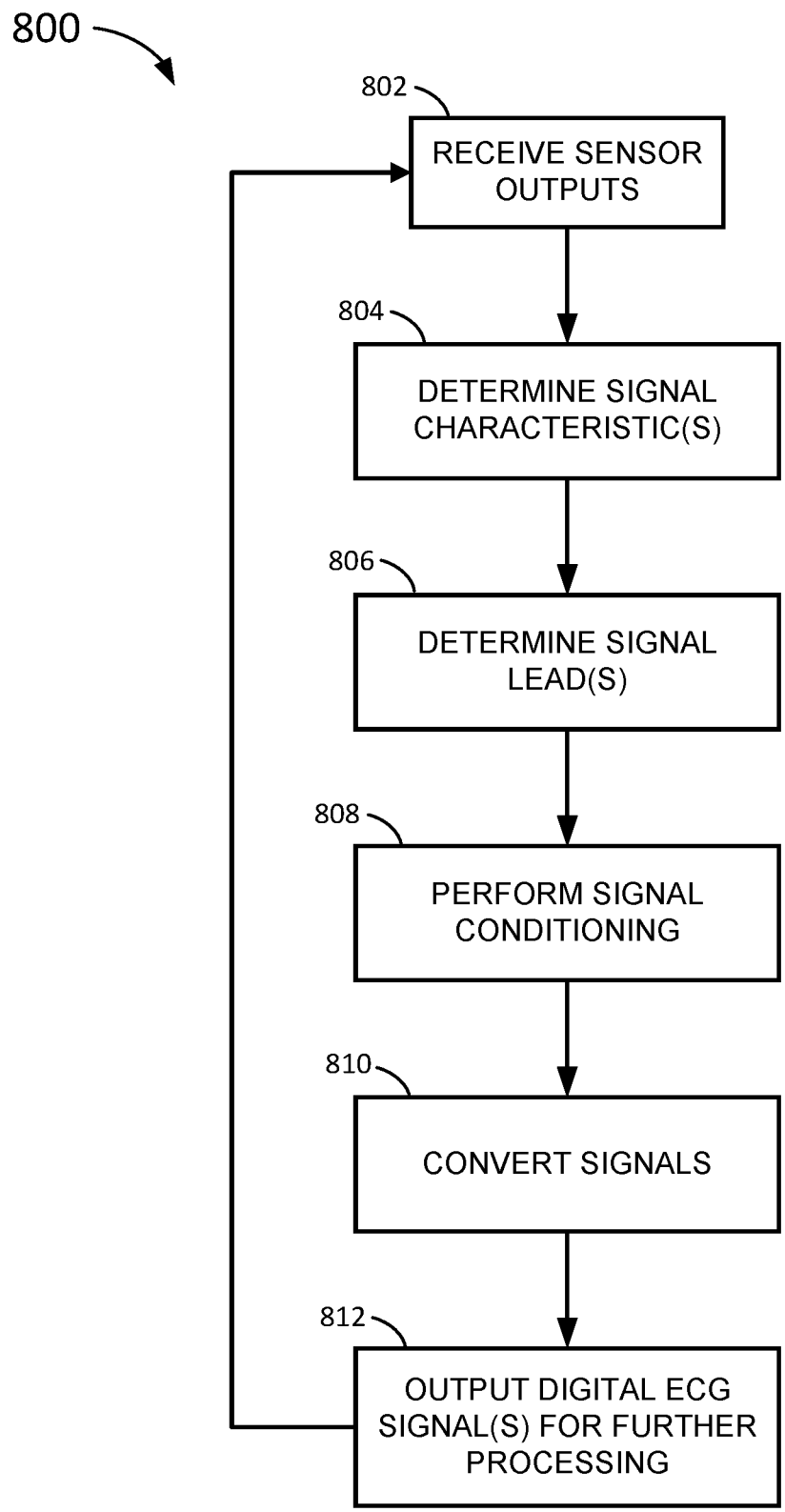
FIG. 8 illustrates a sample process flow for determining sensor leads in accordance with an example of the present disclosure.

FIG. 8 illustrates a sample process 800 that can be used by a processor, such as a processor like the processor 618 has shown in FIG. 6 and discussed above, to analyze sensing electrode signals to determine electrode leads using, for example, the system 700 as shown in FIG. 7 and described above. The processor can receive 802 the outputs of the sensing electrodes. The processor can analyze and process the sensing electrode outputs to determine 804 one or more signal characteristics for each of the sensing electrode outputs. Based upon an analysis of the determined signal characteristics, the processor can determine 806 one or more signal leads for the sensing electrodes. For example, the processor can determine a pair of sensing electrodes that have outputs with similar signal characteristics that would match or otherwise combine to produce a high quality sensing electrode lead.

As further shown in FIG. 8, once the sensing electrode leads are determined, the processor can perform 808 signal conditioning using, for example, one or more operational amplifiers as shown in FIG. 7 and described above. The processor can further convert 810 the conditioned signals using, for example, an analog to digital converter and output 812 the digital signals for further processing.

It should be noted that process 800 includes outputting 812 the digital signals for further processing by way of example only. In certain implementations, the processor performing process 800 can further process the converted signals without outputting to an additional processing device.

Figure 9:
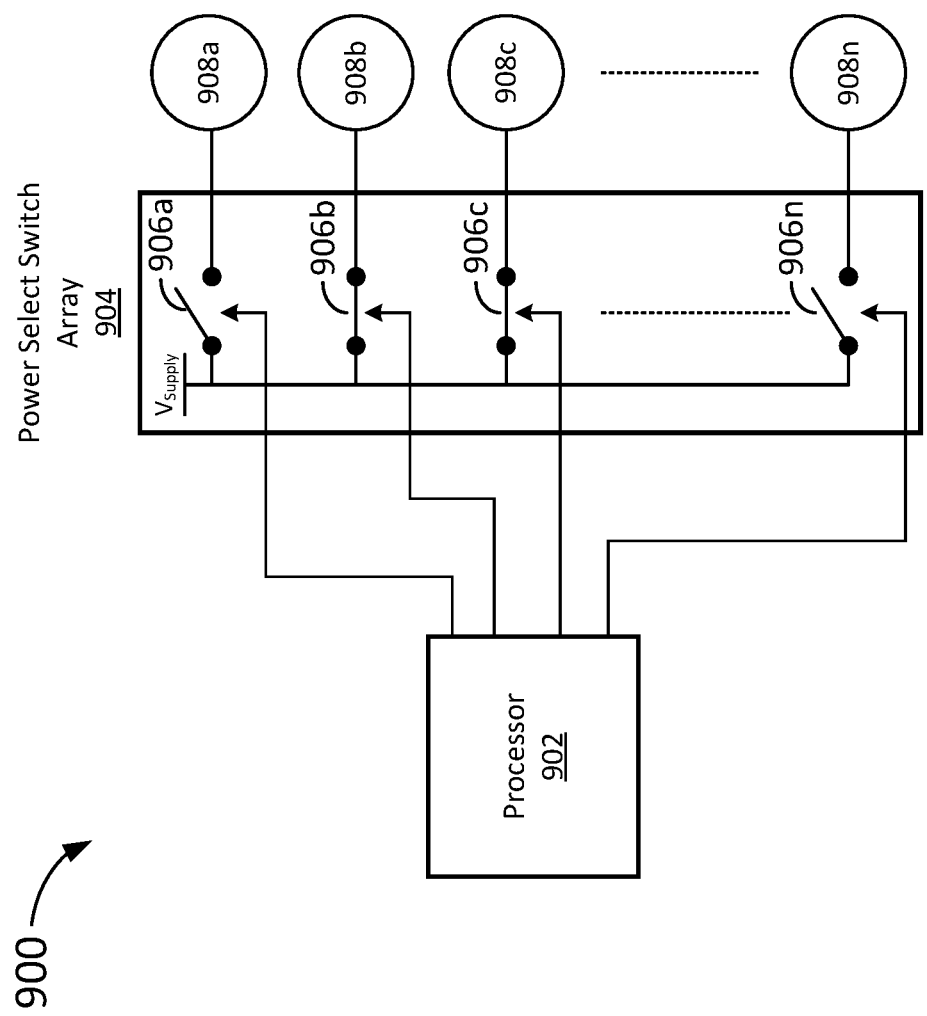
FIG. 9 illustrates a sample system for controlling active sensors in accordance with an example of the present disclosure.

In another example, by monitoring the noise and signal quality at each individual sensing electrode, power to an individual sensing electrode can be reduced or turned off, thereby providing for active power management and power conservation. For example, FIG. 9 illustrates system 900 that includes a power management arrangement for a series of active sensing electrodes as described herein. As shown, a processor 902 can be configured to monitor signal quality and noise for multiple sensing electrodes 908a through 908n. Based upon the signal quality and noise levels of each of the sensing electrodes 908a through 908n, the processor 902 can provide a control signal to one or more individual switches 906a through 906n within a power select switch array 904, thereby turning on or turning off power to one or more of the sensing electrodes 908a through 908n.

For example, as shown in FIG. 9, the processor 902 can determine that the sensing electrode 908b and the sensing electrode 908c are producing high-quality output signals with minimal noise. Similarly, the processor 902 can determine that the sensing electrode 908a and the sensing electrode 908n are producing lower quality output signals with high levels of noise. As such, the processor 902 can control the power select switch array 904 such that: the switch 906a is open, thereby turning off power to the sensing electrode 908a; the switch 906b is closed, thereby providing power to the sensing electrode 908b; the switch 906c is closed, thereby providing power to sensing electrode 908c; and the switch 906n is open, thereby turning off power to sensing electrode 908n.

Figure 10:
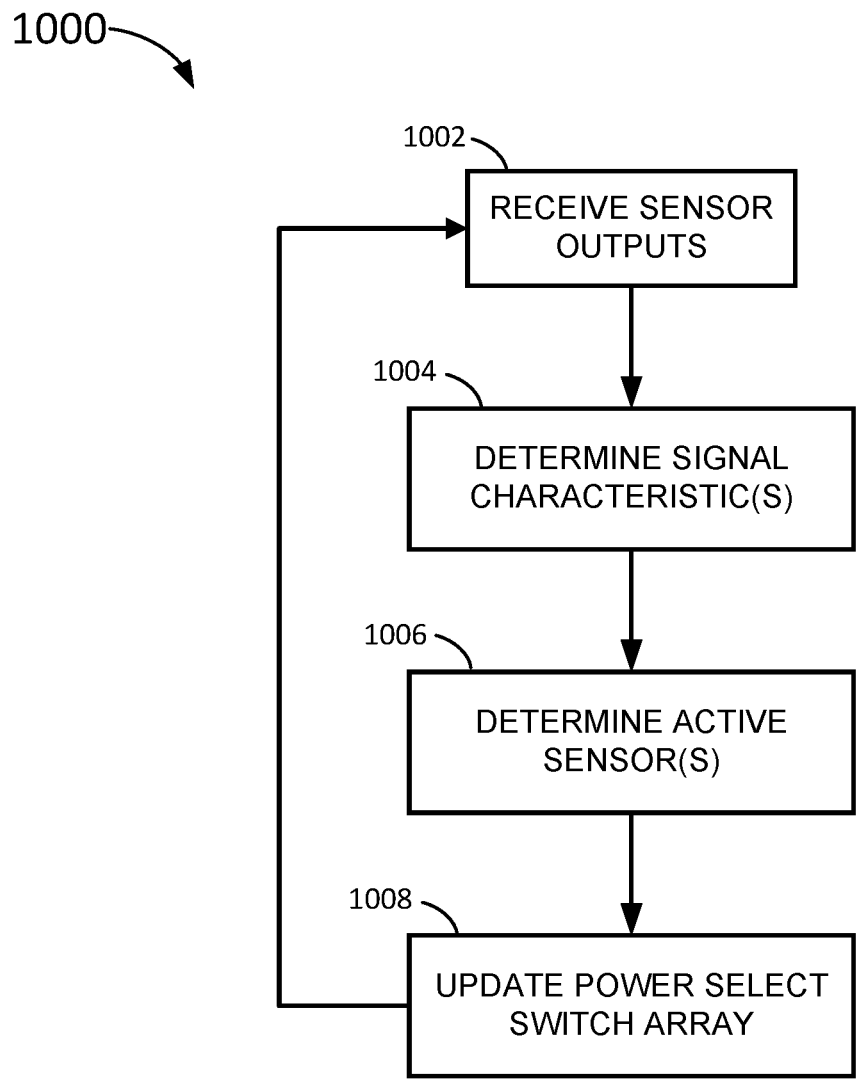
FIG. 10 illustrates a sample process flow for controlling active sensors in accordance with an example of the present disclosure.

FIG. 10 illustrates a sample process 1000 that can be implemented by, for example, a processor such as processor 902 as shown in FIG. 9 and described above. More specifically, process 1000 includes the processor receiving 1002 sensor outputs from each of the sensing electrodes. The processor can determine 1004 signal characteristics for each of the sensor outputs and determine which individual sensing electrodes are producing a high-quality and reliable output signal. For example, the processor can determine a signal-to-noise ratio for each sensor output as received from each sensing electrode. Based upon the determined signal characteristics, the processor can determine 1006 which active sensing electrodes to provide power to and which active sensing electrodes to turn off the power to. For example, the processor can compare the determined signal-to-noise ratio for each sensor output against a threshold value, e.g., a 5:1 signal-to-noise ratio. In certain implementations, the processor can perform a fast Fourier transform-based analysis to look for excess noise (e.g., 60 Hz noise) to determine the suitability of a given sensing electrode. For example, for an output signal that satisfies the threshold and/or further analysis, the processor can determine 1006 to provide power. Conversely, for each output signal that fails to satisfy the threshold, the processor can determine 1006 to turn the power off. Based upon this determination 1006, the processor can update 1008 the power select switch array such that power is delivered to each of the active sensing electrodes appropriately.

It should be noted that analyzing signal-to-noise ratio as described above is provided by way of example only and other signal characteristics can be determined and analyzed. For example, the processor can determine whether a sensor output is indicative of an electrode falloff condition, e.g. that a sensing electrode has lost contact with the patient's body. In such an example, a sensing electrode that has lost contact can be powered off accordingly. In another example, the processor can detect amplifier saturation in the output signal of a sensing electrode. If the output signal is at one of the extremes of an amplifier associated with the sensing electrode, the processor can determine that the amplifier is saturated and that the output signal is not likely useful. In such an example, the processor can turn off power to that sensing electrode.

It should be noted that the system 700 as shown in FIG. 7 and the system 900 as shown in FIG. 9 are provided by way of example only and are intended to show additional functionality that can be achieved using the localized driven ground signals as described herein. Similarly, it should be noted that process 800 as shown in FIG. 8 and process 1000 as shown in FIG. 10 are provided by way of example only to show a set of sample process steps that can be implemented by one or more processors to execute the processes as described herein as related to the systems 700 and 900 as described above.

As described herein, the position of the ECG substrate and the local biasing substrate can vary depending upon the implementation and design of the sensing electrode. FIGS. 11A through 13B describe various implementations and arrangements for a sensing electrode including both an ECG substrate and a biasing substrate as described herein.

Figure 11A:
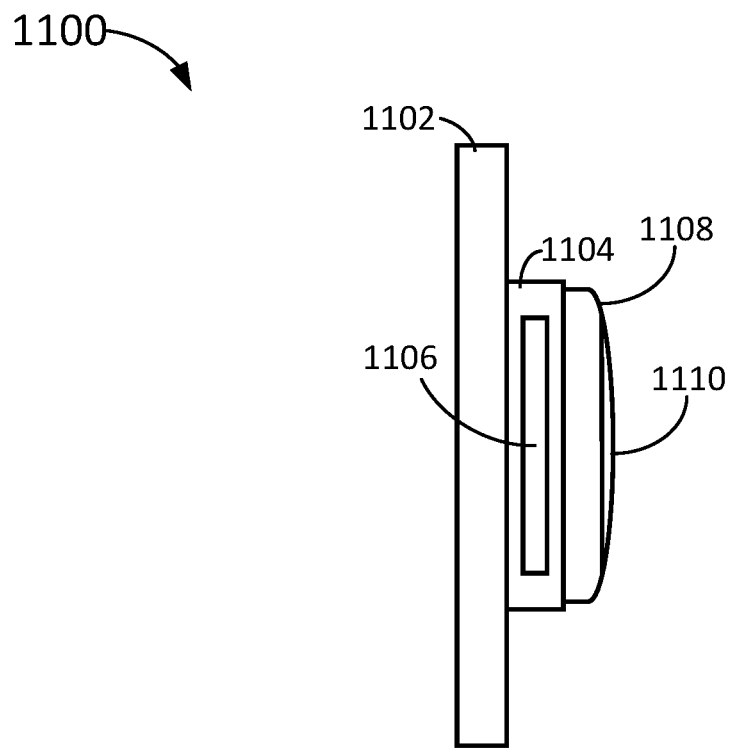
FIGS. 11A and 11B illustrate sample component diagrams of a first arrangement of a sensor having a local driven ground in accordance with an example of the present disclosure.
Figure 11B:
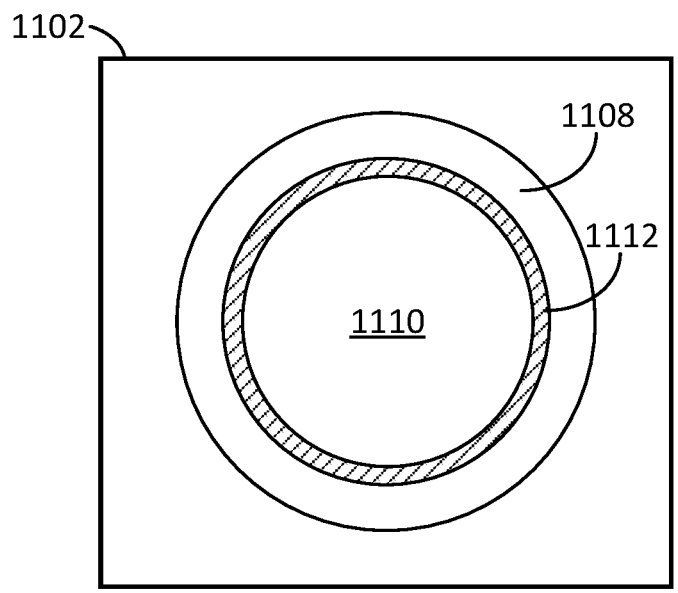

For example, as shown in FIGS. 11A and 11B, the ECG substrate and the biasing substrate can be arranged such that one substrate encircles or otherwise surrounds the other substrate. FIG. 11A illustrates a side view of sensing electrode assembly 1100. As shown in FIG. 11A, the sensing electrode can be connected to a substrate such as a portion of a garment 1102. The assembly 1100 can further include a housing 1104 of the sensing electrode that can be removably attached to the garment 1102. The housing 1104 can also be configured to enclose circuitry 1106. As described herein, the circuitry 1106 can include both ECG sensing circuitry and biasing circuitry as shown, for example, in FIG. 3A as described above. In some examples, the housing 1104 can include a specific ingress protection (IP) rating that classifies the degree of protection the housing provides as defined by international standard EN 60529. For example, the housing 1104 can include an IP rating of at least IP67 which indicates the housing 1104 is dust tight and protected against immersion in water for 30 minutes at depths between 0.15 meters and 1.0 meter. In some examples, the housing 1104 can include an IP rating of at least IP68 which indicates the housing 1104 is dust tight and protected against complete and continuous submersion in water over 1.0 meter in depth.

As further shown in FIG. 11A, the assembly 1100 can further include a first electrode substrate 1108 and a second electrode substrate 1110. In certain implementations, the first electrode substrate 1108 can be configured to function as the ECG substrate as described herein and the second electrode substrate 1110 can be configured to function as the biasing substrate as described herein. In other examples, the first electrode substrate 1108 can be configured to function as the biasing substrate as described herein and the second electrode substrate 1110 can be configured to function as the ECG substrate as described herein.

FIG. 11B illustrates a front view of assembly 1100. For example, as shown in FIG. 11B, the first electrode substrate 1108 is configured to be outside of and to encircle or otherwise surround the second electrode substrate 1110. As further shown in FIG. 11B, an insulating layer 1112 can be positioned between the first electrode substrate 1108 and the second electrode substrate 1110 to provide electrical isolation between the two electrode substrates. For example, the first electrode substrate 1108 can be configured to function as the ECG substrate and can be manufactured from, for example, silver/silver chloride or an oxidized material coated with, for example, a tantalum-oxide coating. The second electrode substrate 1110 can be configured to function as the biasing substrate and can be manufactured from, for example, stainless steel. In such an example, the insulating layer 1112 can be made from a non-conductive material such as rubber, plastic, or another similar insulating material that is sized and configured to electrically isolate the first electrode substrate 1108 from the second electrode substrate 1110. For example, the insulating layer 1112 may be configured and positioned such that the first electrode substrate 1108 and the second electrode substrate 1110 are about 0.01 inches apart, about 0.10 inches apart, about 0.25 inches apart, or about 0.50 inches apart.

Figure 12A:
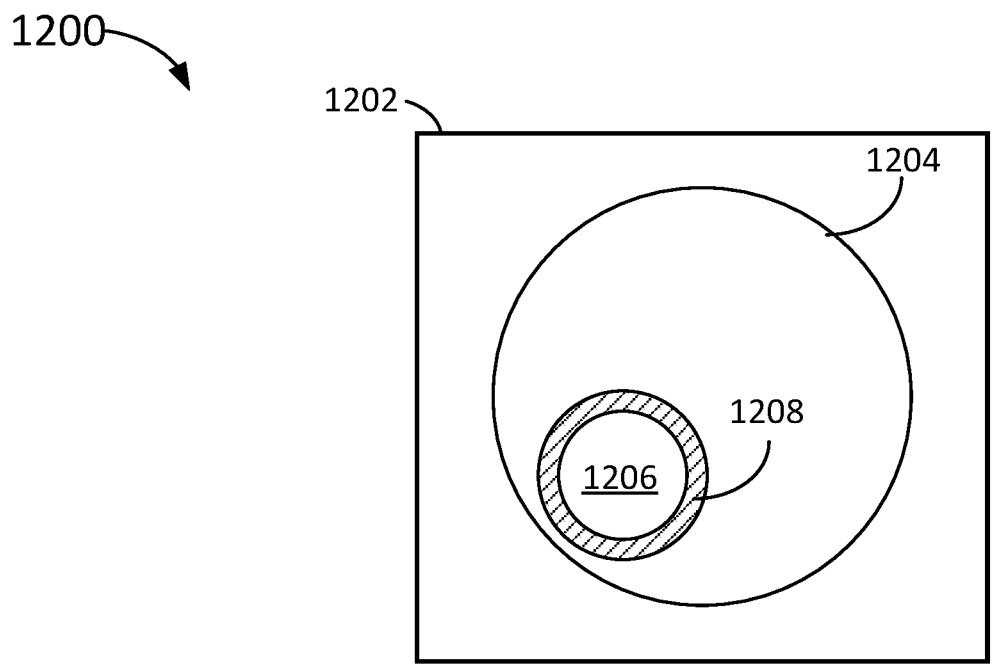
FIGS. 12A and 12B illustrate sample component diagrams of additional arrangements of sensors having a local driven ground in accordance with an example of the present disclosure.
Figure 12B:
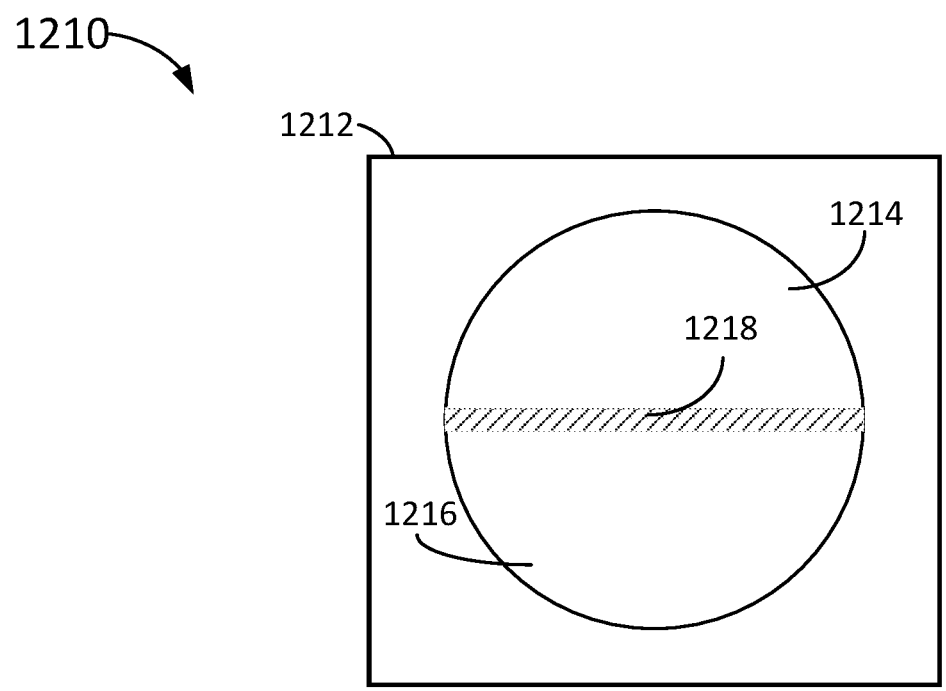

FIGS. 12A and 12B Illustrate alternative arrangements for a sensing electrode including both an ECG substrate and a biasing substrate as described herein. For example, FIG. 12A illustrates sensor assembly 1200 including a sensor mounted on a portion of a garment 1202. As shown in assembly 1200, the sensing electrode includes a first electrode substrate 1204 and a second electrode substrate 1206. Rather than being arranged in concentric circles as shown in FIGS. 11A and 11B, the electrode substrates can be arranged in additional patterns and/or arrangements. For example, as shown in FIG. 12A, the second electrode substrate 1206 can be positioned on one side of the first electrode substrate 1204. As noted above, depending upon the materials used for the first electrode substrate 1204 and the second electrode substrate 1206, the assembly 1200 can further include an insulated layer 1208.

Additionally, rather than surround one electrode substrate with another, the two electrode substrates as described herein can be positioned adjacent to each other. For example, as shown in FIG. 12B, electrode assembly 1210 includes a sensing electrode mounted on a garment 1212. As further shown, the assembly includes a first electrode substrate 1214 positioned adjacent to a second electrode substrate 1216. As further shown, the assembly 1210 can include an insulating layer 1218 positioned between the two electrode substrates and configured to electrically isolate the first electrode substrate 1214 from the second electrode substrate 1216. However, it should be noted that the insulating layer 1218 is shown by way of example only. In certain implementations, the first electrode substrate 1214 and the second electrode substrate 1216 can be spaced apart such that no additional insulating layer is needed to electrically isolate the two electrode substrates. Additionally, it should be noted that the first electrode substrate 1214 and the second electrode substrate 1216 are shown as the same size by way of example only. In implementation, the sizes of the first electrode substrate 1214 and the second electrode substrate 1216 can vary based upon what functionality the electrode substrate is configured to perform. For example, the electrode substrate configured to function as the ECG substrate can have a larger surface area than the electrode substrate configured to function as the biasing substrate.

In certain examples, one or more of the electrode substrates as described herein can be integrated directly into a portion of a garment as a fabric electrode. For example, one or more of the electrode substrates can be integrated as a series of conductive fibers woven into a portion of the garment at a particular location such that, when the garment is worn, the fabric substrates are positioned proximate to the patient's skin.

Figure 13A:
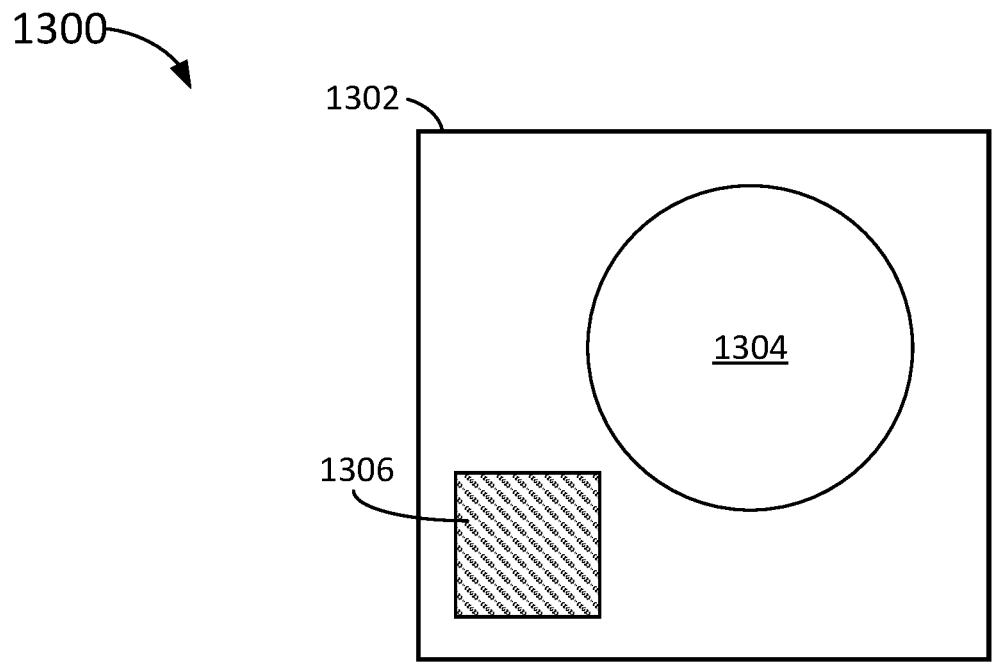
FIGS. 13A and 13B illustrate sample component diagrams of a sensor including one or more fabric sensing components in accordance with an example of the present disclosure.

For example, FIG. 13A illustrates a sensor assembly 1300 including components of a sensing electrode mounted on a portion of a garment 1302. In certain implementations, a first electrode substrate 1304 can be implemented as a metal or otherwise solid electrode substrate removably affixed to the garment 1302. The assembly 1300 can further include a second electrode substrate 1306 that is implemented as a fabric electrode constructed from a conductible fabric material such as a conductive thread woven into a particular pattern on or within the garment 1302. In some examples, the first electrode substrate 1304 can be configured to operate as the ECG substrate. In such an example, the first electrode substrate 1304 can be made from a material such as silver/silver chloride and the second substrate 1306, configured to operate as the biasing substrate, can be made from a material such as a stainless steel thread woven into a particular pattern in or on the garment 1302. In another example, the first substrate 1304 can be configured to operate as the biasing substrate. In such an example, the first electrode substrate 1304 can be implemented as a metal or otherwise solid electrode substrate removably affixed to the garment 1302 and the second substrate 1306, configured to operate as the ECG substrate, can be made from a material such as a silver/silver chloride thread woven into a particular pattern in garment 1302.

Figure 13B:
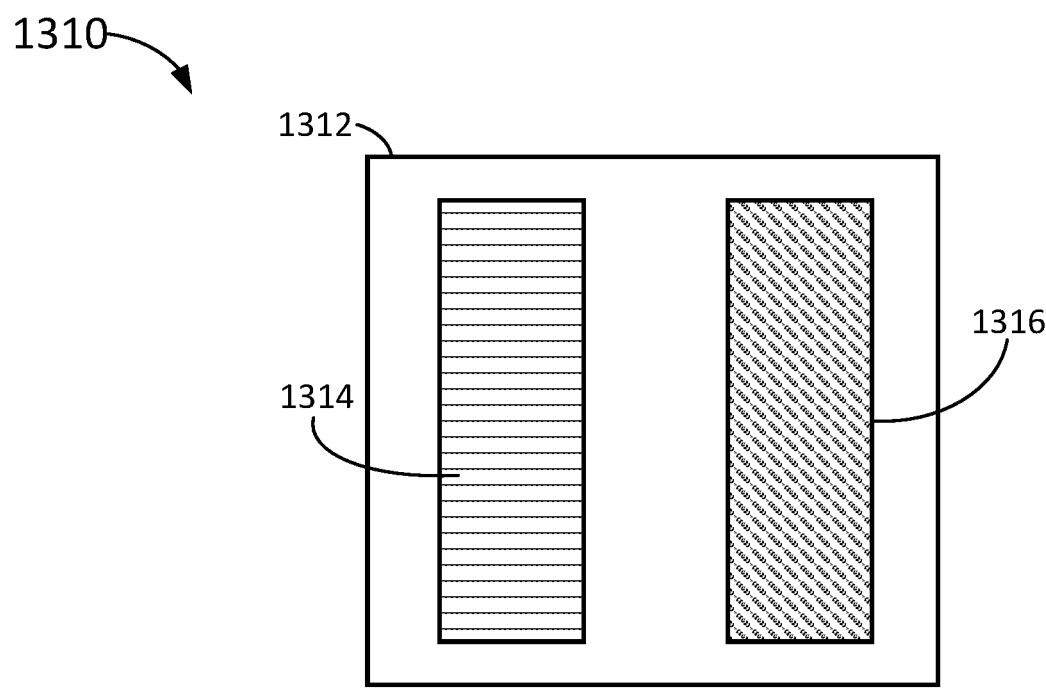

In another example, both the ECG substrate and the biasing substrate in an electrode assembly can be made from conductive fabric materials. For example, FIG. 13B illustrates a sensor assembly 1310 including components of a sensing electrode mounted on a portion of a garment 1312. For example, a first electrode substrate 1314 can be implemented as a fabric electrode constructed from a conductible fabric material such as a conductive thread woven into a particular pattern on garment 1312. Similarly, the assembly 1310 can further include a second electrode substrate 1316 that is implemented as a fabric electrode constructed from a conductible fabric material such as a conductive thread woven into a particular pattern on garment 1312. In some examples, the first electrode substrate 1314 can be configured to operate as the ECG substrate. In such an example, the first electrode substrate 1314 can be made from a material such as a silver/silver chloride thread woven into a particular pattern on the garment 1312. The second substrate 1316, which is configured to operate as the biasing substrate, can be made from a material such as a stainless steel thread woven into a particular pattern in the garment 1312.

In some examples, the first electrode substrate 1314 and the second electrode substrate 1316 can be spaced apart such that the substrates are insulated from each other. For example, the first electrode substrate 1314 and the second electrode substrate 1316 can be spaced apart by about 0.1 inches, 0.25 inches, 0.5 inches, 0.75 inches, 1.0 inch, 1.25 inches, 1.50 inches, or other similar distances.

It should be noted that the position, size, and shape of the electrode substrates as shown in FIGS. 13A and 13B and described above is provided by way of example only. In actual implementation, each of the electrode substrates as described above can be positioned, sized, and shaped based upon an overall design of a wearable medical device garment.

The teachings of the present disclosure can be generally applied to external medical monitoring and/or treatment devices that include one or more sensors as described herein. Such external medical devices can include, for example, ambulatory medical devices as described herein that are capable of and designed for moving with the patient as the patient goes about his or her daily routine. An example ambulatory medical device can be a wearable medical device such as a WCD, a wearable cardiac monitoring device, an in-hospital device such as an HWD, a short-term wearable cardiac monitoring and/or therapeutic device, mobile cardiac event monitoring devices, and other similar wearable medical devices.

The wearable medical device can be capable of continuous use by the patient. In some implementations, the continuous use can be substantially or nearly continuous in nature. That is, the wearable medical device can be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless be considered continuous use. For example, the wearable medical device can be configured to be worn by a patient for as many as 24 hours a day. In some implementations, the patient can remove the wearable medical device for a short portion of the day (e.g., for half an hour to bathe). In such an example, nearly continuous can include 23.5 hours a day of wear with a half hour removal period.

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other healthcare provider (HCP) provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, cardio-vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other non-ECG physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the ambulatory medical devices described herein can be pacing-enabled, e.g., capable of providing therapeutic pacing pulses to the patient. In some examples, the ambulatory medical devices can be configured to monitor for and/or measure ECG metrics including, for example, heart rate (such as average, median, mode, or other statistical measure of the heart rate, and/or maximum, minimum, resting, pre-exercise, and post-exercise heart rate values and/or ranges), heart rate variability metrics, premature ventricular contraction (PVC) burden or counts, atrial fibrillation burden metrics, pauses, heart rate turbulence, QRS height, QRS width, changes in a size or shape of morphology of the ECG information, cosine R-T, artificial pacing, QT interval, QT variability, T wave width, T wave alternans, T-wave variability, and ST segment changes.

As noted above, FIG. 6 illustrates an example component-level view of a medical device controller 600 included in, for example, a wearable medical device. As further shown in FIG. 6, the therapy delivery circuitry 602 can be coupled to one or more electrodes 620 configured to provide therapy to the patient. For example, the therapy delivery circuitry 602 can include, or be operably connected to, circuitry components that are configured to generate and provide an electrical therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuitry and under control of one or more processors (e.g., processor 618) to provide, for example, at least one therapeutic shock to the patient including one or more pacing, cardioversion, or defibrillation therapeutic pulses.

Pacing pulses can be used to treat cardiac arrhythmia conditions such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). In some examples, the capacitors can include a single film or electrolytic capacitor as a series connected device including a bank of the same capacitors. These capacitors can be switched into a series connection during discharge for a defibrillation pulse. For example, a single capacitor of approximately 140 uF or larger, or four capacitors of approximately 650 uF can be used. The capacitors can have a 1600 VDC or higher rating for a single capacitor, or a surge rating between approximately 350 to 500 VDC for paralleled capacitors and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuitry 602 can be configured to perform the switching and pulse delivery operations, e.g., under control of the processor 618. As the energy is delivered to the patient, the amount of energy being delivered can be tracked. For example, the amount of energy can be kept to a predetermined constant value even as the pulse waveform is dynamically controlled based on factors such as the patient's body impedance while the pulse is being delivered.

In certain examples, the therapy delivery circuitry 602 can be configured to deliver a set of cardioversion pulses to correct, for example, an improperly beating heart. When compared to defibrillation as described above, cardioversion typically includes a less powerful shock that is delivered at a certain frequency to mimic a heart's normal rhythm.

The data storage 604 can include one or more of non-transitory computer-readable media, such as flash memory, solid state memory, magnetic memory, optical memory, cache memory, combinations thereof, and others. The data storage 604 can be configured to store executable instructions and data used for operation of the medical device controller 600. In certain examples, the data storage can include executable instructions that, when executed, are configured to cause the processor 618 to perform one or more operations. In some examples, the data storage 604 can be configured to store information such as ECG data as received from, for example, the sensing electrode interface.

In some examples, the network interface 606 can facilitate the communication of information between the medical device controller 600 and one or more other devices or entities over a communications network. For example, where the medical device controller 600 is included in an ambulatory medical device, the network interface 606 can be configured to communicate with a remote computing device such as a remote server or other similar computing device. The network interface 606 can include communications circuitry for transmitting data in accordance with a Bluetooth® wireless standard for exchanging such data over short distances to an intermediary device. For example, such an intermediary device can be configured as a base station, a "hotspot" device, a smartphone, a tablet, a portable computing device, and/or other devices in proximity of the wearable medical device including the medical device controller 600. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain examples, the user interface 608 can include one or more physical interface devices such as input devices, output devices, and combination input/output devices and a software stack configured to drive operation of the devices. These user interface elements can render visual, audio, and/or tactile content. Thus, the user interface 608 can receive input or provide output, thereby enabling a user to interact with the medical device controller 600.

The medical device controller 600 can also include at least one rechargeable battery 610 configured to provide power to one or more components integrated in the medical device controller 600. The rechargeable battery 610 can include a rechargeable multi-cell battery pack. In one example implementation, the rechargeable battery 610 can include three or more 2200 mAh lithium ion cells that provide electrical power to the other device components within the medical device controller 600. For example, the rechargeable battery 610 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 600.

The sensor interface 612 can include physiological signal circuitry that is coupled to one or more sensors configured to monitor one or more physiological parameters of the patient. As shown, the sensors can be coupled to the medical device controller 600 via a wired or wireless connection. The sensors can include one or more ECG sensing electrodes 622, and non-ECG physiological sensors 623 such as vibration sensor 624, tissue fluid monitors 626 (e.g., based on ultra-wide band RF devices), and motion sensors (e.g., accelerometers, gyroscopes, and/or magnetometers). In some implementations, the sensors can include a plurality of conventional ECG sensing electrodes in addition to digital sensing electrodes.

The sensing electrodes 622 can be configured to monitor a patient's ECG information. For example, by design, the digital sensing electrodes 622 can include skin-contacting electrode surfaces that may be deemed polarizable or non-polarizable depending on a variety of factors including the metals and/or coatings used in constructing the electrode surface. All such electrodes can be used with the principles, techniques, devices and systems described herein. For example, the electrode surfaces can be based on stainless steel, noble metals such as platinum, or Ag—AgCl.

In some examples, the electrodes 622 can be used with an electrolytic gel dispersed between the electrode surface and the patient's skin. In certain implementations, the electrodes 622 can be dry electrodes that do not need an electrolytic material. As an example, such a dry electrode can be based on tantalum metal and having a tantalum pentoxide coating as is described above. Such dry electrodes can be more comfortable for long term monitoring applications.

Referring back to FIG. 6, the vibration sensors 624 can be configured to detect cardiac or pulmonary vibration information. For example, the vibration sensors 624 can detect a patient's heart valve vibration information. For example, the vibration sensors 624 can be configured to detect cardio-vibrational signal values including any one or all of S1, S2, S3, and S4. From these cardio-vibrational signal values or heart vibration values, certain heart vibration metrics may be calculated, including any one or more of electromechanical activation time (EMAT), average EMAT, percentage of EMAT (% EMAT), systolic dysfunction index (SDI), and left ventricular systolic time (LVST). The vibration sensors 624 can also be configured to detect heart wall motion, for instance, by placement of the sensor in the region of the apical beat. The vibration sensors 624 can include a vibrational sensor configured to detect vibrations from a patient's cardiac and pulmonary system and provide an output signal responsive to the detected vibrations of a targeted organ, for example, being able to detect vibrations generated in the trachea or lungs due to the flow of air during breathing. In certain implementations, additional physiological information can be determined from pulmonary-vibrational signals such as, for example, lung vibration characteristics based on sounds produced within the lungs (e.g., stridor, crackle, etc.). The vibration sensors 624 can also include a multi-channel accelerometer, for example, a three-channel accelerometer configured to sense movement in each of three orthogonal axes such that patient movement/body position can be detected and correlated to detected cardio-vibrations information. The vibration sensors 624 can transmit information descriptive of the cardio-vibrations information to the sensor interface 612 for subsequent analysis.

The tissue fluid monitors 626 can use RF based techniques to assess fluid levels and accumulation in a patient's body tissue. For example, the tissue fluid monitors 626 can be configured to measure fluid content in the lungs, typically for diagnosis and follow-up of pulmonary edema or lung congestion in heart failure patients. The tissue fluid monitors 626 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 626 can transmit information descriptive of the tissue fluid levels to the sensor interface 612 for subsequent analysis.

As further shown in FIG. 6, the controller 600 can further include an accelerometer interface 630 and a set of accelerometers 632. The accelerometer interface 630 can be operably coupled to each of the accelerometers 632 and configured to receive one or more outputs from the accelerometers. The accelerometer interface 630 can be further configured to condition the output signals by, for example, converting analog accelerometer signals to digital signals (if using an analog accelerometer), filtering the output signals, combining the output signals into a combined directional signal (e.g., combining each x-axis signal into a composite x-axis signal, combining each y-axis signal into a composite y-axis signal, and combining each z-axis signal into a composite z-axis signal). In some examples, the accelerometer interface 630 can be configured to filter the signals using a high-pass or band-pass filter to isolate the acceleration of the patient due to movement from the component of the acceleration due to gravity.

Additionally, the accelerometer interface 630 can configure the output for further processing. For example, the accelerometer interface 630 can be configured to arrange the output of an individual accelerometer 632 as a vector expressing the acceleration components of the x-axis, the y-axis, and the z-axis as received from each accelerometer. The accelerometer interface 630 can be operably coupled to the processor 618 and configured to transfer the output signals from the accelerometers 632 to the processor for further processing and analysis.

As described above, one or more of the accelerometers 632 (e.g., accelerometers 108 as described above) can be integrated into one or more components of a medical device. For example, as shown in FIG. 6, an accelerometer 632 (e.g., accelerometer 108c as described above) can be integrated into the controller 600. In some examples, an accelerometer 632 can be integrated into one or more of a therapy electrode 620, a sensing electrode 622, a physiological sensor 623, and into other components of a medical device. When controller 600 is included in an HWD, an accelerometer can be integrated into an adhesive ECG sensing and/or therapy electrode patch.

In certain implementations, the cardiac event detector 616 can be configured to monitor a patient's ECG signal for an occurrence of a cardiac event such as an arrhythmia or other similar cardiac event. The cardiac event detector can be configured to operate in concert with the processor 618 to execute one or more methods that process received ECG signals from, for example, the sensing electrodes 622 and determine the likelihood that a patient is experiencing a cardiac event. The cardiac event detector 616 can be implemented using hardware or a combination of hardware and software. For instance, in some examples, cardiac event detector 616 can be implemented as a software component that is stored within the data storage 604 and executed by the processor 618. In this example, the instructions included in the cardiac event detector 616 can cause the processor 618 to perform one or more methods for analyzing a received ECG signal to determine whether an adverse cardiac event is occurring. In other examples, the cardiac event detector 616 can be an application-specific integrated circuit (ASIC) that is coupled to the processor 618 and configured to monitor ECG signals for adverse cardiac event occurrences. Thus, examples of the cardiac event detector 616 are not limited to a particular hardware or software implementation.

In some implementations, the processor 618 includes one or more processors (or one or more processor cores) that each are configured to perform a series of instructions that result in manipulated data and/or control the operation of the other components of the medical device controller 600. In some implementations, when executing a specific process (e.g., cardiac monitoring), the processor 618 can be configured to make specific logic-based determinations based on input data received and be further configured to provide one or more outputs that can be used to control or otherwise inform subsequent processing to be carried out by the processor 618 and/or other processors or circuitry with which processor 618 is communicatively coupled. Thus, the processor 618 reacts to specific input stimulus in a specific way and generates a corresponding output based on that input stimulus. In some example cases, the processor 618 can proceed through a sequence of logical transitions in which various internal register states and/or other bit cell states internal or external to the processor 618 can be set to logic high or logic low. As referred to herein, the processor 618 can be configured to execute a function where software is stored in a data store coupled to the processor 618, the software being configured to cause the processor 618 to proceed through a sequence of various logic decisions that result in the function being executed. The various components that are described herein as being executable by the processor 618 can be implemented in various forms of specialized hardware, software, or a combination thereof. For example, the processor 618 can be a digital signal processor (DSP) such as a 24-bit DSP. The processor 618 can be a multi-core processor, e.g., having two or more processing cores. The processor 618 can be an Advanced RISC Machine (ARM) processor such as a 32-bit ARM processor or a 64-bit ARM processor. The processor 618 can execute an embedded operating system, and include services provided by the operating system that can be used for file system manipulation, display & audio generation, basic networking, firewalling, data encryption and communications.

As noted above, an ambulatory medical device such as a WCD can be designed to include a digital front-end where analog signals sensed by skin-contacting electrode surfaces of a set of digital sensing electrodes are converted to digital signals for processing. Typical ambulatory medical devices with analog front-end configurations use circuitry to accommodate a signal from a high source impedance from the sensing electrode (e.g., having an internal impedance range from approximately 100 Kiloohms to one or more Megaohms). This high source impedance signal is processed and transmitted to a monitoring device such as processor 618 of the controller 600 as described above for further processing. In certain implementations, the monitoring device, or another similar processor such as a microprocessor or another dedicated processor operably coupled to the sensing electrodes, can be configured to receive a common noise signal from each of the sensing electrodes, sum the common noise signals, invert the summed common noise signals and feed the inverted signal back into the patient as a driven ground using, for example, a driven right leg circuit to cancel out common mode signals.

Figure 14A:
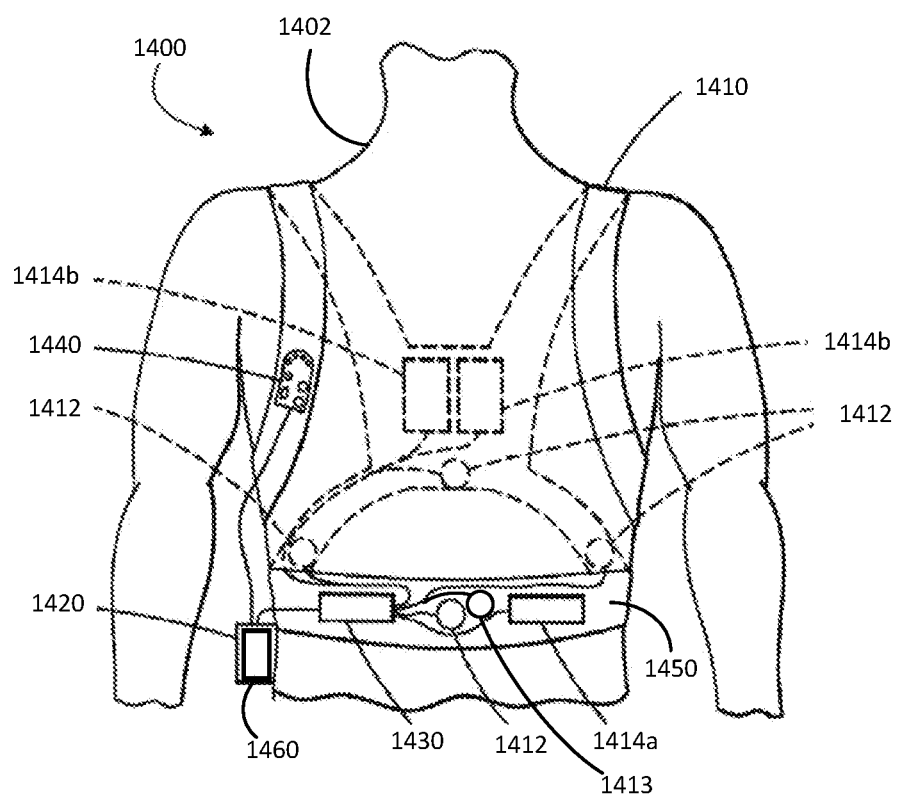

FIG. 14A illustrates an example medical device 1400 that is external, ambulatory, and wearable by a patient 1402, and configured to implement one or more configurations described herein. For example, the medical device 1400 can be a non-invasive medical device configured to be located substantially external to the patient. Such a medical device 1400 can be, for example, an ambulatory medical device that is capable of and designed for moving with the patient as the patient goes about his or her daily routine. For example, the medical device 1400 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 1400 can include one or more of the following: a garment 1410, one or more ECG sensing electrodes 1412, one or more non-ECG physiological sensors 1413, one or more therapy electrodes 1414a and 1414b (collectively referred to herein as therapy electrodes 1414), a medical device controller 1420 (e.g., controller 600 as described above in the discussion of FIG. 6), a connection pod 1430, a patient interface pod 1440, a belt 1450, or any combination of these. In some examples, at least some of the components of the medical device 1400 can be configured to be affixed to the garment 1410 (or in some examples, permanently integrated into the garment 1410), which can be worn about the patient's torso.

The medical device controller 1420 can be operatively coupled to the sensing electrodes 1412, which can be affixed to the garment 1410, e.g., assembled into the garment 1410 or removably attached to the garment, e.g., using hook and loop fasteners. In some implementations, the sensing electrodes 1412 can be permanently integrated into the garment 1410. The medical device controller 1420 can be operatively coupled to the therapy electrodes 1414. For example, the therapy electrodes 1414 can also be assembled into the garment 1410, or, in some implementations, the therapy electrodes 1414 can be permanently integrated into the garment 1410. In an example, the medical device controller 1420 includes a patient user interface 1460 to allow a patient interface with the externally-worn device. For example, the patient can use the patient user interface 1460 to respond to activity related questions, prompts, and surveys as described herein.

Component configurations other than those shown in FIG. 14A are possible. For example, the sensing electrodes 1412 can be configured to be attached at various positions about the body of the patient 1402. The sensing electrodes 1412 can be operatively coupled to the medical device controller 1420 through the connection pod 1430. In some implementations, the sensing electrodes 1412 can be adhesively attached to the patient 1402. In some implementations, the sensing electrodes 1412 and at least one of the therapy electrodes 1414 can be included on a single integrated patch and adhesively applied to the patient's body.

The sensing electrodes 1412 can be configured to detect one or more cardiac signals. Examples of such signals include ECG signals and/or other sensed cardiac physiological signals from the patient. In certain examples, as described herein, the non-ECG physiological sensors 1413 include sensors such as accelerometers, vibrational sensors, RF-based sensors, and other measuring devices for recording additional non-ECG physiological parameters. For example, as described above, the such non-ECG physiological sensors are configured to detect other types of patient physiological parameters and acoustic signals, such as tissue fluid levels, cardio-vibrations, lung vibrations, respiration vibrations, patient movement, etc.

In some examples, the therapy electrodes 1414 can also be configured to include sensors configured to detect ECG signals as well as other physiological signals of the patient. The connection pod 1430 can, in some examples, include a signal processor configured to amplify, filter, and digitize these cardiac signals prior to transmitting the cardiac signals to the medical device controller 1420. One or more of the therapy electrodes 1414 can be configured to deliver one or more therapeutic defibrillating shocks to the body of the patient 1402 when the medical device 1400 determines that such treatment is warranted based on the signals detected by the sensing electrodes 1412 and processed by the medical device controller 1420. Example therapy electrodes 1414 can include metal electrodes such as stainless-steel electrodes that include one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 1414 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device to convert the therapeutic medical device into a monitoring medical device for a specific use (e.g., for operating in a monitoring-only mode) or a patient. Alternatively, the optional therapeutic elements can be deactivated (e.g., via a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 14B:
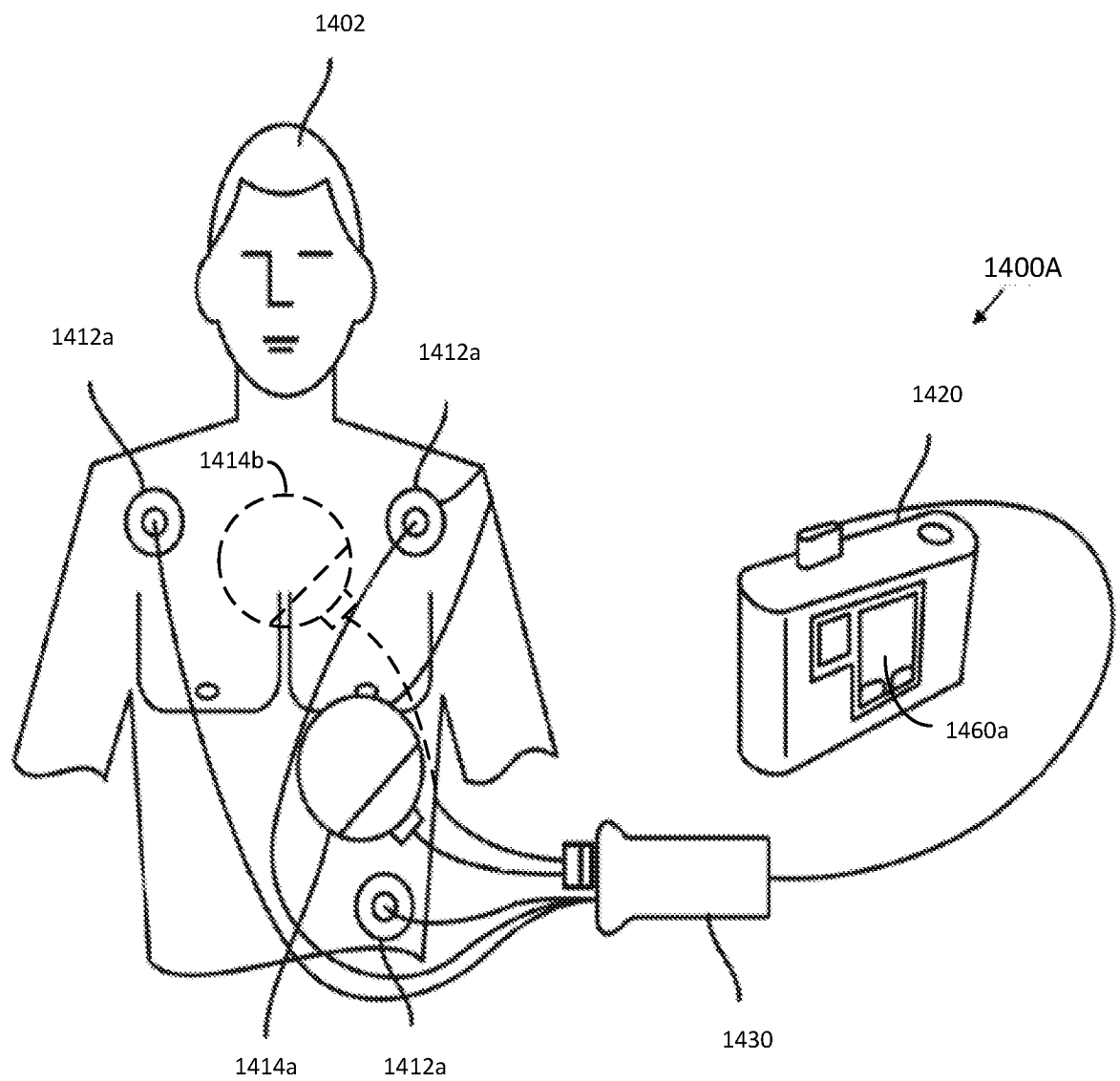

FIG. 14B illustrates a hospital wearable defibrillator 1400A that is external, ambulatory, and wearable by a patient 1402. Hospital wearable defibrillator 1400A can be configured in some implementations to provide pacing therapy, e.g., to treat bradycardia, tachycardia, and asystole conditions. The hospital wearable defibrillator 1400A can include one or more ECG sensing electrodes 1412a, one or more therapy electrodes 1414a and 1414b, a medical device controller 1420 and a connection pod 1430. For example, each of these components can be structured and function as like number components of the medical device 1400. For example, the electrodes 1412a, 1414a, 1414b can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. For example, the front adhesively attachable therapy electrode 1414a attaches to the front of the patient's torso to deliver pacing or defibrillating therapy. Similarly, the back adhesively attachable therapy electrode 1414b attaches to the back of the patient's torso. In an example scenario, at least three ECG adhesively attachable sensing electrodes 1412a can be attached to at least above the patient's chest near the right arm, above the patient's chest near the left arm, and towards the bottom of the patient's chest in a manner prescribed by a trained professional.

A patient being monitored by a hospital wearable defibrillator and/or pacing device may be confined to a hospital bed or room for a significant amount of time (e.g., 75% or more of the patient's stay in the hospital). As a result, a user interface 1460a can be configured to interact with a user other than the patient, e.g., a nurse, for device-related functions such as initial device baselining, setting and adjusting patient parameters, and changing the device batteries.

In some examples, the hospital wearable defibrillator 1400A can further include one or more motion sensors such as accelerometers. For example, an accelerometer can be integrated into one or more of a sensing electrode 1412a (e.g., integrated into the same patch as the sensing electrode), a therapy electrode 1414a (e.g., integrated into the same patch as the therapy electrode), the medical device controller 1420, the connection pod 1430, and various other components of the hospital wearable defibrillator 1400A.

In some implementations, an example of a therapeutic medical device that includes a digital front-end in accordance with the systems and methods described herein can include a short-term defibrillator and/or pacing device. For example, such a short-term device can be prescribed by a physician for patients presenting with syncope. A wearable defibrillator can be configured to monitor patients presenting with syncope by, e.g., analyzing the patient's physiological and cardiac activity for aberrant patterns that can indicate abnormal physiological function. For example, such aberrant patterns can occur prior to, during, or after the onset of syncope. In such an example implementation of the short-term wearable defibrillator, the electrode assembly can be adhesively attached to the patient's skin and have a similar configuration as the hospital wearable defibrillator described above in connection with FIG. 14A.

Figure 14D:
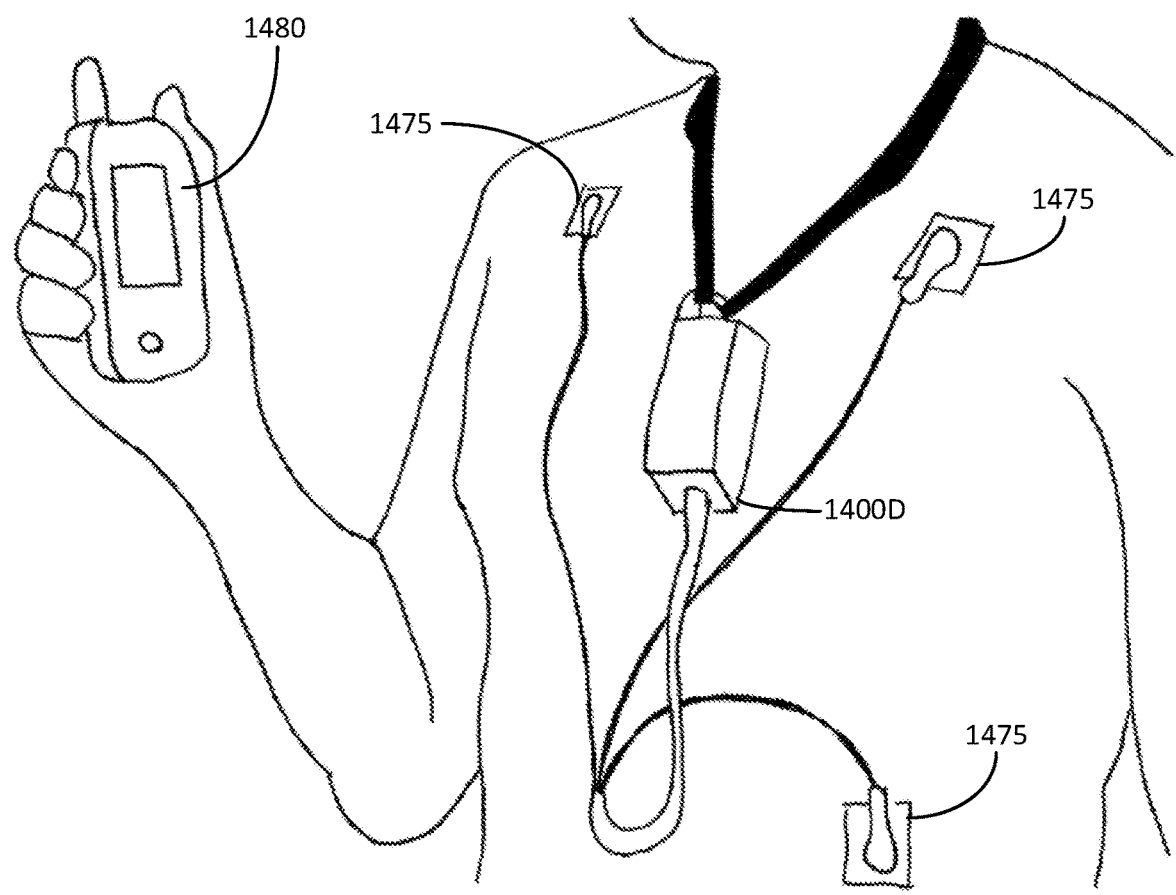

FIGS. 14C and 14D illustrate example wearable patient monitoring devices with no treatment or therapy functions. For example, such devices are configured to monitor one or more physiological parameters of a patient, e.g., for remotely monitoring and/or diagnosing a condition of the patient. For example, such physiological parameters can include a patient's ECG information, tissue (e.g., lung) fluid levels, cardio-vibrations (e.g., using accelerometers or microphones), and other related cardiac information. A cardiac monitoring device is a portable device that the patient can carry around as he or she goes about their daily routine.

Referring to FIG. 14C, an example wearable patient monitoring device 1400C can include tissue fluid monitors 1465 that use RF based techniques to assess fluid levels and accumulation in a patient's body tissue. Such tissue fluid monitors 1465 can be configured to measure fluid content in the lungs, typically for diagnosis and follow-up of pulmonary edema or lung congestion in heart failure patients. The tissue fluid monitors 1465 can include one or more antennas configured to direct RF waves through a patient's tissue and measure output RF signals in response to the waves that have passed through the tissue. In certain implementations, the output RF signals include parameters indicative of a fluid level in the patient's tissue. In examples, device 1400C may be a cardiac monitoring device that also includes digital sensing electrodes 1470 for sensing ECG activity of the patient. Device 1400C can pre-process the ECG signals via one or more ECG processing and/or conditioning circuits such as an ADC, operational amplifiers, digital filters, signal amplifiers under control of a microprocessor. Device 1400C can transmit information descriptive of the ECG activity and/or tissue fluid levels via a network interface to a remote server for analysis. Additionally, in certain implementations, the device 1400C can include one or accelerometers for measuring motion signals as described herein.

Referring to FIG. 14D, another example wearable cardiac monitoring device 1400D can be attached to a patient via at least three adhesive digital cardiac sensing electrodes 1475 disposed about the patient's torso. Additionally, in certain implementations, the device 1400D can include one or accelerometers integrated into, for example, one or more of the digital sensing electrodes for measuring motion signals as described herein.

Cardiac devices 1400C and 1400D are used in cardiac monitoring and telemetry and/or continuous cardiac event monitoring applications, e.g., in patient populations reporting irregular cardiac symptoms and/or conditions. These devices can transmit information descriptive of the ECG activity and/or tissue fluid levels via a network interface to a remote server for analysis. Example cardiac conditions that can be monitored include atrial fibrillation (AF), bradycardia, tachycardia, atrio-ventricular block, Lown-Ganong-Levine syndrome, atrial flutter, sino-atrial node dysfunction, cerebral ischemia, pause(s), and/or heart palpitations. For example, such patients may be prescribed a cardiac monitoring for an extended period of time, e.g., 10 to 30 days, or more. In some ambulatory cardiac monitoring and/or telemetry applications, a portable cardiac monitoring device can be configured to substantially continuously monitor the patient for a cardiac anomaly, and when such an anomaly is detected, the monitor can automatically send data relating to the anomaly to a remote server. The remote server may be located within a 24-hour manned monitoring center, where the data is interpreted by qualified, cardiac-trained reviewers and/or HCPs, and feedback provided to the patient and/or a designated HCP via detailed periodic or event-triggered reports. In certain cardiac event monitoring applications, the cardiac monitoring device is configured to allow the patient to manually press a button on the cardiac monitoring device to report a symptom. For example, a patient can report symptoms such as a skipped beat, shortness of breath, light headedness, racing heart rate, fatigue, fainting, chest discomfort, weakness, dizziness, and/or giddiness. The cardiac monitoring device can record predetermined physiologic parameters of the patient (e.g., ECG information) for a predetermined amount of time (e.g., 1-30 minutes before and 1-30 minutes after a reported symptom). As noted above, the cardiac monitoring device can be configured to monitor physiologic parameters of the patient other than cardiac related parameters. For example, the cardiac monitoring device can be configured to monitor, for example, cardio-vibrational signals (e.g., using accelerometers or microphones), pulmonary-vibrational signals, breath vibrations, sleep related parameters (e.g., snoring, sleep apnea), tissue fluids, among others.

In some examples, the devices described herein (e.g., FIGS. 14A-14D) can communicate with a remote server via an intermediary or gateway device 1480 such as that shown in FIG. 14D. For instance, devices such as shown in FIGS. 14A-D can be configured to include a network interface communications capability as described herein in reference to, for example, FIG. 6.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the scope of the appended claims. For example, it is to be understood that the present disclosure contemplates that, to the extent possible, one or more features of any embodiment can be combined with one or more features of any other embodiment.

Other examples are within the scope of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. An ambulatory cardiac device for improving a signal to noise profile of an ECG signal of a patient, the ambulatory cardiac device comprising:
   a garment configured to be worn about a torso of the patient; and
   a plurality of active electrocardiogram (ECG) electrodes configured to be disposed in a plurality of locations about the patient, each active ECG electrode comprising
   an ECG electrode substrate configured to be in physical contact with skin of the patient,
   a local biasing substrate proximate to the ECG electrode substrate and configured to be in physical contact with the skin of the patient,
   local biasing circuitry that is electrically connected to the local biasing substrate, wherein the local biasing circuitry is configured to provide a local biasing signal into a body of the patient via the local biasing substrate, and
   a housing that is removably attached to the garment, encloses the local biasing circuitry, and holds the local biasing substrate,
   wherein the garment is configured to hold the plurality of active ECG electrodes in contact with the skin of the patient when the patient wears the garment.

2. The ambulatory cardiac device of claim 1, further comprising ECG sensing circuitry configured to sense a surface electrical signal from at least one of the ECG electrode substrates, the surface electrical signal including at least a portion of at least one of the local biasing signals.

3. The ambulatory cardiac device of claim 2, further comprising a processor operably connected to the ECG sensing circuitry and configured to:
   receive the surface electrical signal from the ECG sensing circuitry; and
   determine the ECG signal of the patient based at least in part on the surface electrical signal received from the ECG sensing circuitry.

4. The ambulatory cardiac device of claim 1, wherein at least one of the local biasing circuitries is configured to apply a constant biasing signal to the body of the patient.

5. The ambulatory cardiac device of claim 4, wherein the constant biasing signal has a voltage of one of about 0.5 volts, about 1.0 volt, about 1.5 volts, about 2.0 volts, about 2.5 volts, about 3.0 volts, about 3.5 volts, about 4.0 volts, or about 4.5 volts.

6. The ambulatory cardiac device of claim 4, wherein the housing is rated as IP67 in accordance with standard EN 60529 in effect on the filing date of this application.

7. The ambulatory cardiac device of claim 4, further comprising at least one controller operably coupled to the plurality of active ECG electrodes, the at least one controller configured to determine an arrhythmia condition based on the ECG signal of the patient.

8. The ambulatory cardiac device of claim 7, further comprising a therapy electrode for delivering one or more therapeutic pulses to the patient based on the determined arrhythmia condition.

9. The ambulatory cardiac device of claim 1, wherein at least one of the local biasing circuitries is configured to apply a time-varying biasing signal based upon at least a portion of a surface electrical signal sensed from a particular one of the ECG electrode substrates.

10. The ambulatory cardiac device of claim 9, wherein the time-varying biasing signal comprises at least one of a time-varied current or a time-varied voltage.

11. The ambulatory cardiac device of claim 10, wherein a particular one of the plurality of active ECG electrodes comprises signal processing circuitry configured to determine noise included in the surface electrical signal sensed from the particular ECG electrode.

12. The ambulatory cardiac device of claim 11, wherein the time-varying biasing signal is based upon the determined noise included in the surface electrical signal sensed from the particular ECG electrode.

13. The ambulatory cardiac device of claim 11, further comprising a processor configured to determine the ECG signal of the patient, wherein the signal processing circuitry is configured to cancel the noise from the surface electrical signal prior to the processor determining the ECG signal of the patient.

14. The ambulatory cardiac device of claim 11, wherein the signal processing circuitry comprises a filter and amplifier circuit to process the surface electrical signal sensed from the particular ECG electrode to isolate the noise.

15. The ambulatory cardiac device of claim 9, wherein each housing is disposed proximate to the ECG electrode substrate for housing the ECG electrode substrate, the housing rated as IP67 in accordance with standard EN 60529 in effect on the filing date of this application.

16. The ambulatory cardiac device of claim 1, wherein at least one of the local biasing signals is configured to provide a grounding signal to the body of the patient to reduce noise in a surface electrical signal sensed from at least one of the ECG electrode substrates.

17. The ambulatory cardiac device of claim 1, wherein
   a particular one of the plurality of active ECG electrodes further comprises an analog-to-digital converter operably coupled to the ECG electrode substrate of the particular one of the plurality of active ECG electrodes,
   the ambulatory cardiac device further comprises ECG sensing circuitry configured to sense a surface electrical signal from the ECG electrode substrate of the particular one of the plurality of active ECG electrodes, and the analog-to-digital converter is configured to convert at least a portion of the surface electrical signal to a digital surface electrical signal.

18. The ambulatory cardiac device of claim 1, wherein each of the plurality of active ECG electrodes comprises a dry ECG electrode.

19. The ambulatory cardiac device of claim 1, wherein at least one of the local biasing substrates substantially surrounds at least one of the ECG electrode substrates.

20. The ambulatory cardiac device of claim 1, further comprising:
- a shared driven ground electrode configured to aggregate surface electrical signals sensed from two or more of the ECG electrode substrates; and
- common mode rejection circuitry configured to derive a common mode rejection signal from the aggregated surface electrical signals and inject the common mode rejection signal into the body of the patient.

* * * * *